US012006275B2

(12) United States Patent
Meckler et al.

(10) Patent No.: US 12,006,275 B2
(45) Date of Patent: Jun. 11, 2024

(54) PROCESS FOR MAKING LEVOAMPHETAMINE

(71) Applicant: CHEMAPOTHECA, LLC, Delmar, NY (US)

(72) Inventors: Harold Meckler, Delmar, NY (US); Praveen Suryadevara, Raleigh, NC (US); Marcus Brackeen, Raleigh, NC (US); Darryl Cleary, Raleigh, NC (US)

(73) Assignee: Pharmapotheca A, Inc., Wilmington, DE (US)

( * ) Notice: Subject to any disclaimer, the term of this patent is extended or adjusted under 35 U.S.C. 154(b) by 401 days.

(21) Appl. No.: 17/435,881

(22) PCT Filed: Mar. 2, 2020

(86) PCT No.: PCT/US2020/020713
§ 371 (c)(1),
(2) Date: Sep. 2, 2021

(87) PCT Pub. No.: WO2020/180825
PCT Pub. Date: Sep. 10, 2020

(65) Prior Publication Data
US 2022/0162153 A1 May 26, 2022

Related U.S. Application Data

(60) Provisional application No. 62/813,033, filed on Mar. 2, 2019.

(51) Int. Cl.
C07C 209/62 (2006.01)
C07C 209/86 (2006.01)
C07F 9/22 (2006.01)
C07F 9/564 (2006.01)
G01N 33/94 (2006.01)

(52) U.S. Cl.
CPC .......... C07C 209/62 (2013.01); C07C 209/86 (2013.01); C07F 9/222 (2013.01); C07F 9/564 (2013.01); G01N 33/946 (2013.01)

(58) Field of Classification Search
CPC ... C07C 209/62; C07C 209/86; C07C 211/27; C07F 9/222; C07F 9/564; C07F 9/2408; C07F 9/242; C07F 9/2475; G01N 33/946; C07B 2200/07
See application file for complete search history.

(56) References Cited

U.S. PATENT DOCUMENTS

| 6,399,828 | B1 | 6/2002 | Boswell |
| 7,662,787 | B2 | 2/2010 | Mickle |
| 7,705,184 | B2 | 4/2010 | Buenger |
| 8,487,134 | B2 | 7/2013 | Meudt |
| 9,278,904 | B2 | 3/2016 | Meckler |
| 9,321,794 | B2 | 4/2016 | Meckler |
| 9,657,041 | B2 | 5/2017 | Meckler |
| 10,087,202 | B2 | 10/2018 | Meckler |
| 11,123,310 | B2 | 9/2021 | Popp |
| 2017/0210768 | A1* | 7/2017 | Meckler ............... C07C 209/62 |

FOREIGN PATENT DOCUMENTS

| FR |  | 59265 | 4/1969 |
| WO | WO 2007/054105 |  | 5/2007 |
| WO | WO 2011/084098 |  | 7/2011 |

OTHER PUBLICATIONS

Kojima, Scifinder Cas Registry 1485-13-8 for 2-methyl-3-phenyl-aziridine, Kojima 1959 et al.
Allen and Ely, Synthetic Methods for Amphetamines, Crime Scene magazine, p. 15-25 Spring 2011.
Angew Alkylation of Diethyl Phosphoramidates—A Simple Route from Primary to Secondary Amines, Chem Int ed 1977.
Mekenyan, Scifinder 2010:1165579 ACS, Aziridine Use of Genotoxicity Information . . . , Chem Res Tox vol. 23 Issue 10 pp. 1519-1540, 2010.
Sakurai, Scifinder 2000-630740 ACS, Aziridine Recommendation of Occupational exposure limits, J Occup Health, vol. 42, Issue 4, pp. 213-228, 2000.
Koleva, Scifinder 2011-1058228 ACS, Modelling of Acute Oral . . . aziridine toxicity, Toxicology InVitro, vol. 25, Issue 7, pp. 1281-1293, 2011.
Lambrechts, Leuckart-specific impurities in amphetamine, Bulletin on Narcotics, UNODC Everywhere, pp. 47-57, Jan. 1, 1984.
D'Ambra, Scifinder Search Results for D'Ambra patents (allergy drugs, regioselectivity) Accession 2002-52000, from US20020007068, 1999.
Rege et al. Drug Metabolism and Disposition, vol. 30 No. 12, pp. 1337-1343, Irreversible Inhibition of CYP2D6 by (−) Chloroephedrine (impurity), 2002.
EMEA Committee for Medical Products, Grignard Solvents Committee, Feb. 10, 2005, pp. 1-7.
FDA CDER Guidance for Industry, (genotox guidance) Dec. 2008.
Skinner, Methamphetamine Synthesis via Hydriodic . . . , Forensic Sci Int'l, 48 (1990) 123-134, red phos method.
Anderson, Development of a Harmonised Method for Profiling . . . , Forensic Sci Int'l 169 (2007) pp. 50-63, GC method.
Anderson, Development of a Harmonised Method for Profiling . . . , Forensic Sci Int'l 169 (2007) pp. 64-76, GC method.
Stojanovska, A Review of Impurity Profiling . . . , Forensic Sci Int'l 224 (2013) 8-26.
Power, An Unusual Presentation of Customs Seizure, Forensic Sci Int'l 234 (2014) e10-e13.
Barker, A Study of the Use of Ephedra, Forensic Sci Int'l 166 (2007) 102-109.
Humfrey, Keeping Afloat in a Sea of Impurities, Global Safety Assessment, Astra Zeneca Jul. 6, 2007.
EMEA Solvent (Grignard) impurities, ICH Topic Q3C (R4), pp. 1-22, 2010.
Funel and Abele, Diels Alder Reactions Part 1, Angewandte Reviews, Angew. Chem Int 2013 vol. 52, 1-44, 2013.

(Continued)

Primary Examiner — Sudhakar Katakam
(74) Attorney, Agent, or Firm — Juneau & Mitchell; Todd L. Juneau

(57) ABSTRACT

This is invention is related to processes for synthesis of levoamphetamine derivatives and novel intermediates thereby, and processes for using the same.

20 Claims, No Drawings

(56) References Cited

OTHER PUBLICATIONS

Funel and Abele, Diels Alder Reactions Part 3, Angewandte Reviews, Angew. Chem Int 2013 vol. 52, 1-44, 2013.
Funel and Abele, Diels Alder Reactions Part 2, Angewandte Reviews, Angew. Chem Int 2013 vol. 52, 1-44, 2013.
Funel and Abele, Diels Alder Reactions Part 4, Angewandte Reviews, Angew. Chem Int 2013 vol. 52, 1-44, 2013.
Stephans, Substituted Aziridines, Prep and Properties, J Chem Engin, vol. 8, No. 4, pp. 625-626, Oct. 1963.
Stephans, Relative rates of Reaction and Direction of Ring Opening, J Chem Engin, vol. 14, No. 1, pp. 114-115, Jan. 1969.
Borkovec, Insect Chemosterilants, Aziridnylphosphine Oxides, JMedChem vol. 9, pp. 522-526, Feb. 1966.
Hata, Fragmentation Reaction of Ylide, JACS vol. 98-19, pp. 6033-6036, Sep. 1976.
Poshkus, the Reaction of Neutral Esters of Trivalent Phosphorus Acids, JACS vol. 79, pp. 6127-6129, 1957.
Jessing, Aziridines in Synthesis, Baran Lab Jan. 2007.
Hassner, Ring Opening of Aziridine Phosphonates, JOC vol. 41, pp. 2273-2276, 1976.
Stromberg, Comparative GC Analysis, J Chromatography 106 (1975) 335-342, amphet sulfate.
Lambrechts, Profiling of Impurities in Illicit Amphetamine, 1986 J Chromatography vol. 369 (1976) pp. 365-377 HPLC impurities.
Allen, Methamphetamines from Ephedrine, J Forensic Sci vol. 32, No. 4, Jul. 1987, pp. 953-962.
Milstein, Friedel Crafts Reactions of Htree Member Heterocycles, J Het Chem vol. 5, pp. 339-241, Mar. 1968.
Hassner, Regiospecificity: A Useful Terminology, JOC vol. 33, No. 7 pp. 2684-2686 Jul. 1968.
Todd, Aneurin, A Synthesis of Thiochrome, J Chem Soc 1936, pp. 1601-1605.
Hider, Prep of Evidence in Amphet Prosecutions, J Forensic Sci pp. 75-79 1960's.
Anandasankar, Scifinder 7763-71-5, referring to WO 2011 130726, priority to US 2011-32804, and 2010-61325236.
Osowska-Pacewicka, N-Phosphorylated Aziridines—new reagents for electrophilic amination, Polish J Chem 68-6 pp. 1263-1264 1994.
Pramanik, An Efficient Scalable Process for Benzphetamine HCI, JACS J Org Process Res Dev 2014 vol. 18 pp. 495-500.
Giles, A Improved Process for the N-Alkylation of Indoles Using Chiral N-Protected 2-Mehtylaziridines J. Org Proc Res Dev, 2003 vol. 7, pp. 22-24.
Snodin, Potentially Mutagenic Impurities, J Org Process Res Dev 2014, vol. 18, pp. 836-839 Racemic.
Raman, Regulatory Expectations Towards Genotoxic, J Org Process Res Dev 2014 vol. 18 pp. 834-835.
Teasdale, Regulatory Highlights, J Org Process Res Dev 2014 vol. 18, 458-472.
Jawahar, Direct Stereospecific Synthesis of Unprotected N—H and N—Me Aziridines from Olefins, Sciences 343, 61 pp. 61-65, 2014.
Koziara, A.; Oleiniczak, B.; Osowska, K.; Zwierzak, A. "Phosphoramidomercuration-Demercuration: A Simple Two-Step Conversion of Alkenes into Alkanamines" *Synthesis* 1982, 918-920.
Osowska-Pacewicka, Reactions of N-Phosphorylated Aziridines with Dianions Derived from Ethyl Aceotacetate and 1,3 Diketones, Synth. Commun. Org. Chem. vol. 28:7, 1127-1137 1998.
Gajda, Synthesis of Primary sec-Alkylamines via Nucleophilic Ring-opening of N-Phosphorylated Aziridines, Tetrahedron Letters, 53:13, 4935-4946 1997.
Hassner, A.; Galle, J. E.; "Ring Opening of Aziridine Phosphonates. Correlation of Structure, Nuclear Magnetic Resonance Spectra and Reactivity" *J. Org. Chem.*, 1976, 41, 2273-2276.
Breque, A .; Savignac P.; "Derives Phosphoryles des Methyl-1 et Methyl-2 Amino-2 Ethanethiols" *Phosphorus and Sulfur*. 1980, 89-94.
US Pharmacopeia; "Dextroamphetamine Sulfate Tablets" *Official Monographs*. 2014, 2570-2571.
Herbrink, M.; Thijssen, B.; Hillebrand, M.J.X.; Rosing, H.; Schellen, J.H.M.; Nuijen, B.; Beijnen, J.H.; "Development and validation of a high-performance liquid chromatography-tandem mass spectrometry assay for the quantification of Dexamphetamine in human plasma" *Journal of Pharmaceutical and Biomedical Analysis*. 2018. 259-264.
WO 2015/130660 Int'l Search Report—citing Zwierzak, Synthesis Comm., Phosphor-amido-mercuration, pp. 918, Nov. 1982; Zwierzak, Tetrahedron Letters, Synthesis of Primary sec-Alkylamines, 53:13, 4935, 1997; and Li Xinyao, Synthesis, An Improved and Mild Wenker Synthesis of Aziridines, vol. 20, 3423, 2010, abstract, scheme 2, dated Jun. 25, 2015, Chemapotheca.
WO 2015/130660 Int'l Written Opinion of '660 ISR, dated Jun. 25, 2015, Chemapotheca.
WO 2015/130661 Int'l Search Report—Zwierzak, Synthesis Comm., Phosphor-amido-mercuration, pp. 918, Nov. 1982; Aesengi phD Thesis, Asymmetric Synthesis of 2-Substituted-Aminotetralins, Norway Univ Sci Tech, Nov. 2010, Scheme 1,4; and Li Xinyao, Synthesis, An Improved and Mild Wenker Synthesis of Aziridines, vol. 20, 3423, 2010, abstract, scheme 2, dated Jun. 25, 2015, Chemapotheca.
WO 2015/130661 Int'l Written Opinion of '661 ISR, dated Jun. 29, 2015, Chemapotheca.
WO 2020/180825 Int'l Prelim. Report on Patentability, dated Aug. 25, 2021, Chemapotheca.
WO 2020/180825 Int'l Search Report, dated Mar. 2, 2020, Chemapotheca.
WO 2020/180825 Search Question, dated Oct. 6, 2020, Chemapotheca.
WO 2020/180825 Int'l Search Report, dated Oct. 6, 2020, Chemapotheca.

* cited by examiner

PROCESS FOR MAKING LEVOAMPHETAMINE

BACKGROUND

Field of the Invention

This is invention is related to processes for synthesis of levoamphetamine derivatives and novel intermediates thereby.

Background of the Invention

L-amphetamine sulfate is used in a mixture of enantiomers of 1-phenyl-2-aminopropane salts as an active pharmaceutical agent for treatment of attention deficit hyperactivity disorder (ADHD) and narcolepsy. L-amphetamine sulfate has also been researched to improve cognition in multiple sclerosis (MS) patients.

One problem with levoamphetamine synthesis is that amphetamines have a stereo-defined amine center, which can be subject to racemization. Accordingly, only stereospecific methods are useful. However, stereospecific methods do not provide the economic requirements of high yields, high selectivity and low process costs. Typically such reactions involve a coupling agent, such as Grignard or organolithium reagents. Conventional teaching requires that the use such organometallics requires that the reaction temperature be maintained at a cold temperature, such as an ice bath at less than 10 degrees Celsius.

Another problem with levoamphetamine synthesis is that the intermediates are toxic as well as flammable. This requires special handling such as double-walled drums and safety accommodations to protect manufacturing personnel.

The prior art in U.S. Pat. No. 6,399,828 teaches the production of amphetamine using various methods. In one approach norephedrine is refluxed with hydrogen iodide and red phosphorous. In another approach norephedrine is chlorinated using thionyl chloride and then catalytically hydrogenated. In U.S. Pat. No. 7,705,184, amphetamine synthesis is disclosed using hydrogenation of a chlorinated phenylpropanolamine. Aziridine chemistry, and specifically aziridine phosphoramidates are not taught in the amphetamine synthesis prior art.

Zwierzak et al. disclose a method of reacting N-phosphorylated aziridines with copper-modified Grignard reagents as a new route to substituted pyrrolines and pyrrolidines. However, Zwierzak et al discloses this method as being regiospecific, which it is not. Int'l J. for Rapid Commun. of Syn. Org. Chem., 28:7, 1127-1137 (1998). Accordingly, where the prior art contained an erroneous teaching, it was surprising to discover otherwise.

Additionally, the use of protecting groups and leaving groups is well known. However, it has been discovered that there is significant variation among the various protecting groups. Specifically, where a carbonyl is used as a protecting group, the reaction must be kept at below −10 degrees Celsius or the carbonyl will react with the Grignard reagent. Where a sulfonyl is used as a protecting group, it is impossible to remove the protecting group without destroying the molecule.

Accordingly, there is a need for synthetic processes and useful compounds for the manufacture of levoamphetamine and its derivatives which have high purity, high chemical yield, high selectivity, low cost, lower toxicity and are less dangerous to handle.

BRIEF SUMMARY OF THE INVENTION

The present invention addresses one or more of the shortcomings of the prior art by providing processes for the synthesis of levoamphetamine, derivatives, including salts, solvates, hydrates, and novel precursors and intermediates obtained thereby, by synthesizing aziridine phosphoramidate compounds in specified solvents at specified temperatures, and then converting to a novel aryl or aryl-alkyl phosphoramidate precursors using a modified organometallic compound such as a organocopper reagent, where the novel aryl or aryl-alkyl phosphoramidate precursor is then easily converted to the target compounds using known reactions, e.g. acidification, methylation of the nitrogen followed by dephosphorylation, etc.

In one preferred aspect the invention provides a synthetic pathway to levoamphetamine derivatives using an aziridine based process with an organometallic compound by heating the reactants in a first step, and then adding as a second step the Grignard reagent in a dosage controlled fashion.

In another preferred embodiment, the invention provides a process of making levoamphetamine sulfate, said process comprising:

providing a compound of Formula 5 having a regioisomeric purity >99%:

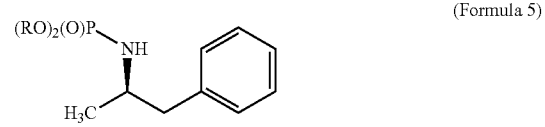

(Formula 5)

wherein R is alkyl or aryl; and deprotecting the compound of Formula 5 under acidic conditions effective to produce levoamphetamine free base and then levoamphetamine sulfate of Formula I:

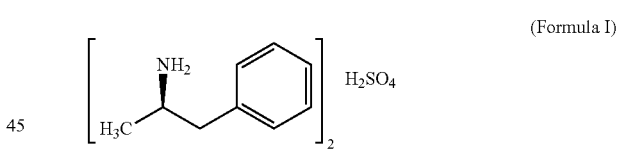

(Formula I)

wherein the step of providing a compound of Formula 5 comprises the steps of: providing a compound of Formula 4:

(Formula 4)

wherein R is alkyl or aryl and reacting the compound of Formula 4 with phenylmagnesium halide and a copper catalyst under solvent and temperature conditions effective to produce a compound of Formula 5 having a regioisomeric purity >99% and stereochemical purity of >99%, wherein the solvent conditions comprise a crystallization step requiring a mixture of two or more solvents, wherein one of the two or more solvents is residue THF.

In another preferred embodiment, the invention provides a process as described above wherein the acidic conditions are aqueous hydrochloric, sulfuric or phosphoric acids.

In another preferred embodiment, the invention provides a process as described above wherein the aqueous acid water content is in an amount of 50% to 90%.

In another preferred embodiment, the invention provides a process as described above wherein R=methyl, ethyl, isopropyl or phenyl.

In another preferred embodiment, the invention provides a process as described above, wherein said providing a compound of Formula 5 comprises:

providing a compound of Formula 4:

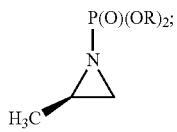

wherein R is alkyl or aryl and reacting the compound of Formula 4 with phenylmagnesium halide and a copper or copper halide catalyst under solvent and temperature conditions effective to produce a compound of Formula 5 in a purity substantially free of any regioisomeric and stereochemical impurities.

In another preferred embodiment, the invention provides a process as described above to produce Formula 5 wherein the regioisomeric purity of Formula 5 is >99% and the regioisomer is <0.1%.

In another preferred embodiment, the invention provides a process as described above to produce Formula 5 wherein the stereoisomeric purity of formula 5 is >99% and the stereoisomer is <0.1%.

In another preferred embodiment, the invention provides a process as described above to produce Formula 5 wherein the R=methyl, ethyl, isopropyl or phenyl.

In another preferred embodiment, the invention provides a process as described above to produce Formula 5 wherein the copper catalyst is CuCl, CuCl2, CuBr CuF, Cu(OAc)2, Cu(acac)2, Cu(OMe)2, Copper turnings or Copper nanoparticles.

In another preferred embodiment, the invention provides a process as described above to produce Formula 5 wherein one of the mixture of two or more solvents is selected from the group consisting of heptanes, an organic ether, tetrahydrofuran, 2-methyltetrahydrofuran or toluene.

In another preferred embodiment, the invention provides a process as described above to produce Formula 5 wherein said temperature conditions range from 25° C. to 80° C.

In another preferred embodiment, the invention provides a process as described above, wherein said providing a compound of Formula 4 comprises: providing a compound of Formula 3

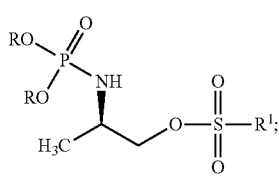

wherein R is alkyl or aryl; R1 is alkyl or aryl or substituted aryl and reacting the compound of Formula 3 with a base under conditions effective to produce a compound of Formula 4.

In another preferred embodiment, the invention provides a process as described above for producing Formula 4 where R1=alkyl aryl or substituted aryl In another preferred embodiment, the invention provides a process as described above for producing Formula 4 where R1 is selected from the group of methyl, phenyl or 4-methylphenyl.

In another preferred embodiment, the invention provides a process as described above for producing Formula 4 where R1 is methyl.

In another preferred embodiment, the invention provides a process as described above for producing Formula 4 wherein R1=methyl and R=methyl, ethyl, isopropyl or phenyl.

In another preferred embodiment, the invention provides a process as described above for producing Formula 4, wherein the base is potassium hydroxide or potassium carbonate.

In another preferred embodiment, the invention provides a process as described above for producing Formula 3, wherein the step of providing a compound of Formula 3 comprises the steps of: providing a compound of Formula 2

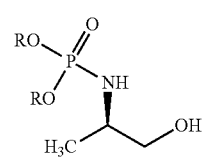

(Formula 2)

wherein R is alkyl or aryl; and reacting the compound of Formula 2 with an alkyl, aryl or substituted arylsulfonyl chloride and a base under conditions effective to produce a compound of Formula 3.

In another preferred embodiment, the invention provides a process as described above for producing Formula 3 wherein the R=methyl, ethyl, isopropyl or phenyl.

In another preferred embodiment, the invention provides a process as described above for producing Formula 2, wherein said providing a compound of Formula 2 comprises: providing a compound of Formula 1

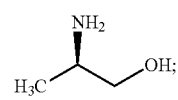

(Formula 1)

and reacting the compound of Formula 1 with

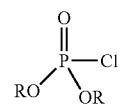

wherein R=alkyl or aryl
under conditions effective to produce a compound of Formula 2.

In another preferred embodiment, the invention provides a process as described above for producing Formula 2 wherein the R=methyl, ethyl, isopropyl or phenyl.

In another preferred embodiment, the invention provides a compound of formula:

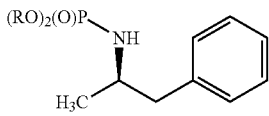

Prepared as per claim 5 in a regiochemical purity of >1700:1

Wherein:

R is alkyl or aryl

In another preferred embodiment, the invention provides a compound prepared according to claim 5, wherein the alkyl group is selected from the group consisting of methyl, ethyl or isopropyl In another preferred embodiment, the invention provides a compound prepared according to claim 5 wherein the aryl group is phenyl.

In another preferred embodiment, the invention provides a compound of formula:

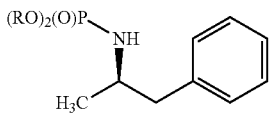

Prepared as per claim 5 in a stereochemical purity of >1000:1

Wherein:

R is alkyl or aryl

In another preferred embodiment, the invention provides a compound prepared according to claim 5, wherein the alkyl group is selected from the group consisting of methyl, ethyl or isopropyl In another preferred embodiment, the invention provides a compound prepared according to claim 5 wherein the aryl group is phenyl.

In another preferred embodiment, the invention provides a compound of the formula:

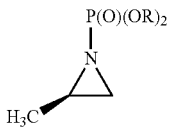

wherein: R is alkyl or aryl.

In another preferred embodiment, the invention provides an aziridine compound as described above, wherein the alkyl group is selected from the group consisting of methyl, ethyl or isopropyl.

In another preferred embodiment, the invention provides an aziridine compound as described above, wherein the aryl group is phenyl.

In another preferred embodiment, the invention provides a process for the synthesis of levoamphetamine derivatives comprising the step of performing a stereospecific cuprate addition reaction upon an aziridine phosphoramidate compound to obtain a chiral aryl or aryl-alkyl phosphoramidate levoamphetamine precursor.

In another preferred embodiment, the invention provides a process for solvent extraction of compounds 5a-d from a mixture of compounds 5a-d and 6a-d, comprising the step of performing a solvent extraction using a mixture of two or more solvents wherein at least one of the two or more solvents is THF.

In another embodiment, the invention includes a process for assaying a sample, comprising the steps: (i) obtaining a plasma sample of a patient; (ii) performing a suitable assay for amphetamine and impurities; (iii) identifying whether the plasma sample contains an impurity of Compound 6b from a cuprate process or has one or more impurities from a Leuckart and/or nitrostyrene processes said impurities comprising cathinone, benzaldehyde, related compound A or B, or unspecified/formaldehyde impurity, wherein the cuprate process comprises preparing dextroamphetamine (sulfate) using a cuprate reaction of a phosphoramidate compound in the presence of a Grignard reagent, followed by hydroxide reduction of the alkyl side chain, followed by a first solvent crystallization in THF and heptanes, and a second solvent recrystallization in heptanes, made into a sulfate salt; (iv) comparing the impurity in plasma sample results to a reference standard for the impurity of Compound 6b in the cuprate process and from the Leuckart and/or nitrostyrene processes comprising cathinone, benzaldehyde, related compound A or B, or unspecified/formaldehyde impurity; and (v) identifying whether the amphetamine from the plasma sample was prepared using the cuprate process.

DETAILED DESCRIPTION OF THE INVENTION

Accordingly, the present invention relates to processes for the synthesis of levoamphetamine, derivatives of these, including their salts, solvates, hydrates and novel precursors and intermediates obtained thereby, by synthesizing aziridine phosphoramidate compounds in specified solvents at specified temperatures, and then converting to a novel aryl or aryl-alkyl phosphoramidate precursor using an organometallic compound such as a copper salt, where the novel aryl or aryl-alkyl phosphoramidate precursor is then easily converted to the target compounds using known reactions, e.g. acid dephosphorylation, methylation of the nitrogen followed by acid dephosphorylation, etc.

Levo rotation refers to optical rotation. The optical rotation of D-alaninol is −17 to −18 degrees. The optical rotation of L-alaninol is +17 to +18 degrees.

Alkyl means any C1-C10 straight or branched chain alkyl, wherein said alkyl, is optionally substituted with C1-C6 alkyl, C2-C6 alkenyl, hydroxy, amino, halo, haloalkyl, thiocarbonyl, ester, thioester, alkoxy, alkenoxy, cyano, nitro, imino, alkylamino, aminoalkyl, sulfhydryl, thioalkyl, or sulfonyl.

Aryl means any alicyclic or aromatic, mono-, bi- or tricyclic, carbo- or heterocyclic ring, wherein the ring is either unsubstituted or substituted with one or more substituent(s) independently selected from the group including, but not limited to, alkylamino, amido, amino, aminoalkyl, azo, benzyloxy, C1-C9 straight or branched chain alkyl, C1-C9 alkoxy, C2-C9 alkenyloxy, C2-C9 straight or branched chain alkenyl, C3-C8 cycloalkyl, C5-C7 cycloalkenyl, carbonyl, carboxy, cyano, diazo, ester, formanilido, halo, haloalkyl, hydroxy, imino, isocyano, isonitrilo, nitrilo, nitro, nitroso, phenoxy, sulfhydryl, sulfonylsulfoxy, thio, thioalkyl, thiocarbonyl, thiocyano, thioester, thioformamido, trifluoromethyl, and carboxylic and heterocyclic moieties, including alicyclic and aromatic structures; wherein the individual ring size is 5-8 members; wherein said heterocyclic ring contains 1-6 heteroatom(s) independently selected from the group consisting of O, N, and S; and wherein said aromatic or tertiary alkyl amine is optionally oxidized. Useful carbo- and heterocyclic rings include without limitation phenyl, benzyl, naphthyl, indenyl, azulenyl, fluorenyl, anthracenyl, indolyl, isoindolyl, indolinyl, benzofuranyl, benzothiophenyl, indazolyl, benzimidazolyl, benzthiazolyl, tetrahydrofuranyl, tetrahydropyranyl, pyridyl, pyrrolyl, pyrrolidinyl, pyridinyl, pyrimidinyl, purinyl, quinolinyl, isoquinolinyl, tetrahydroquinolinyl, quinoliziny1, furyl, thiophenyl, imidazolyl, oxazolyl, benzoxazolyl, thiazolyl, isoxazolyl, isotriazolyl, oxadiazolyl, triazolyl, thiadiazolyl, pyridazinyl, pyrimidinyl, pyrazinyl, triazinyl, trithianyl, indolizinyl, pyrazolyl, pyrazolinyl, pyrazolidinyl, thienyl, tetrahydroisoquinolinyl, cinnolinyl, phthalazinyl, quinazolinyl, quinoxalinyl, naphthyridinyl, pteridinyl, carbazolyl, acridinyl, phenazinyl, phenothiazinyl, and phenoxazinyl.

R may also be in certain preferred embodiments any C2-C10 straight or branched chain alkenyl or C1-C10 alkoxy, unsubstituted or optionally substituted with moieties listed above.

Copper nanoparticles means particles having an average diameter of about 1 nm-100 nm.

Alkyl Phosphonic Acid Protecting group means any group attached to the aziridine nitrogen having one or more alkyl groups attached to a phosphorous atom thereby having the formula P—O—(OR)2, where R1 and R2 can be the same or different, and include without limitation any alkyl, alkoxy or aryl group as defined herein, and including any and all equivalents thereof.

Solvents, as used and exemplified herein, are not intended to be limiting and may include without limitation solvents selected from Ligroine, Pentane, Hexane, Heptane, Octane, Cyclopentane, Cyclohexane, Cycloheptane, Cyclooctane, Dichloromethane, Chloroform, Carbon tetrachloride, 1,2-Dichloroethane, 1,1,2,2-Tetrachloroethane, Methylacetate, Ethylacetate, Propylacetate, Butylacetate, Dimethylformamide, Diethylformamide, Dimethylacetamide, Diethylacetamide, Diethylether, Diisopropylether, 20 methyl tert-Butyl ether, THF, Dioxane, Acetonitrile, Sulfolane, DMSO, HMPT, NMP or mixtures of these solvents. Preferred solvents are Dichloromethane, Chloroform, Ethyl acetate, Propyl acetate, Butyl acetate, Dimethylformamide, Diethylformamide, Dimethylacetamide, Diethylacetamide, Diisopropylether, methyl tert-Butyl ether, THF, Dioxane, Acetonitrile or mixtures of these. Especially preferred solvents are Dichloromethane, Chloroform, Ethyl acetate, Butyl acetate, Dimethylformamide, Dimethylacetamide, methyl tert-Butyl ether, THF, Dioxane, Acetonitrile or mixtures of these.

The term, regioselective or regioselectivity, means without limitation, by way of explanation, the preference of one direction of chemical bond making or breaking over all other possible directions. It can often apply to which of many possible positions a reagent will affect, such as which proton a strong base will abstract from an organic molecule, or where on a substituted benzene ring a further substituent will add. Because of the preference for the formation of one product over another, the reaction is selective. This reaction is regioselective because it selectively generates one constitutional isomer rather than the other.

The term, stereoselective or stereoselectivity, means without limitation, by way of explanation, the property of a chemical reaction in which a single reactant forms an unequal mixture of stereoisomers during the non-stereospecific creation of a new stereocenter or during the non-stereospecific transformation of a pre-existing one. The selectivity arises from differences in steric effects and electronic effects in the mechanistic pathways leading to the different products.

The literature teaches that the product from the cuprate addition to the aziridine phosphoramidate is regiospecific which has been discovered, is not the case. In fact, the crude product is of acceptable purity to proceed with. Further, it has also been discovered that, where the process generates 3-5% of 6 (a,b,c or d) in the crude product, that it could not be removed later in the synthetic sequence. It was also found that if you used a single solvent (5b crystallizes from heptane or petroleum ether), then you did not remove the corresponding 6b. It is required to leave a residue of the reaction solvent (THF) in the mixture to separate the 5b from 6b. Interestingly, it has been discovered that a ratio of specific solvents yielded the most preferred embodiment. This ratio comprises about 7 part heptane and 1 part THF for 5b, and the other versions of 5 (a, c or d) needed other solvent mixtures, but the common item was that it was required to leave a residue of THF in the mixture.

Experimental Introduction:

Unless otherwise noted, reagents and solvents were used as received from commercial suppliers.

NMR spectra: Proton nuclear magnetic resonance spectra were obtained on a Bruker AV 300 or a Bruker AV 500 spectrometer at 300 MHz and 500 MHz, respectively. Spectra are given in ppm ($\delta$) and coupling constants, J, are reported in Hertz. Tetramethylsilane was used as an internal standard for proton spectra.

HPLC analyses (achiral): Analyses were obtained on a Varian Prostar 210 HPLC system using a Prevail C18 column (53×7 mm, Alltech) with PDA detection at 208-210 nm and solvent gradient program Method A.

HPLC Method A:

| Time (mm) | Flow (mL/min) | % A | % B |
|---|---|---|---|
| 0.0 | 2.0 | 95.0 | 5.0 |
| 10.0 | 2.0 | 5.0 | 95.0 |
| 11.5 | 2.0 | 5.0 | 95.0 |
| 11.6 | 2.0 | 95.0 | 5.0 |
| 13.0 | 2.0 | 95.0 | 5.0 |

A = Water with 0.05% v/v Trifluoroacetic Acid
B = Acetonitrile with 0.05% v/v Trifluoroacetic Acid HPLC analyses (chiral method 1): Analyses were obtained using a CR(−) CrownPak (150×4 mm, 5 um, Diacil Lot #CRM0CB-OK005) with PDA detection at 210-215 nm and isocratic solvent 90% water pH=1.5 (perchloric acid): 10% Methanol; Flow rate: 0.7 mL/min.

HPLC analysis (chiral method 2): 5 Analyses were obtained using a CHIRALPAK® IA-3 (50×4.6 mm i.d., 3 μm) with PDA detection at 205 nm and isocratic 0.1% Formic Acid in H2O/ACN=70/30; 1.0 mL/min.

GC (FID):

| Column | Agilent HP-5 ms UI 30 m × 0.32 mm × 0.25 μm PN: 123-1334 |
|---|---|

-continued

| | | |
|---|---|---|
| Injection Volume | 1 μL | |
| Carrier Gas | Helium | |
| Constant flow rate | 1 mL/min (13.5 psi initial @ 80° C.) | |
| Inlet Temp | 250° C. | |
| Split Ratio | 20:1 | |
| Detector Temp | 300° C. | |
| H2 Flow | 40 mL/min | |
| Air Flow | 450 mL/min | |
| He Makeup Flow | 45 mL/min | |
| Oven Ramp | 80° C. Initial 10° C./min to 180° C. 5° C./min to 240° C. hold for 3 min | |
| Total Runtime | 25 minutes | |

| CAP-0104 | CAP-0105 | CAP-0106 |
|---|---|---|
| RRT = 0.47 | RRT = 1 | RRT = 1.02-1.03 |

Samples are prepared at 2 mg/mL in chloroform.

Preparation of Compound 4 (Scheme 1)

| 4 | R | % Yield |
|---|---|---|
| a | Me | 76 |
| b | Et | 80 |
| c | iPr | 42 |
| d | Ph | 60 |

Preparation of 4a:

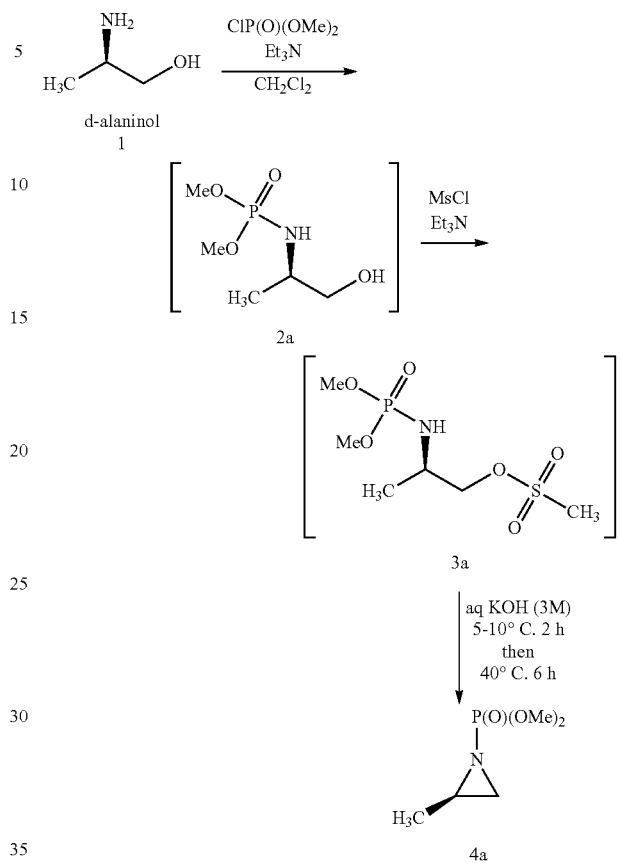

A 500 mL, 3-neck flask equipped with an overhead mechanical stirrer and pressure equalizing addition funnel was charged with 1 (d-alaninol; 12.5 g, 166.4 mmol), triethylamine (29 mL, 208 mmol, 1.25 equiv) and dichloromethane (125 mL). The reaction solution was cooled to +2° C. and treated with dimethylphosphoryl chloride (20 mL, 183 mmol, 1.10 equiv) over 40 minutes while maintaining an internal temperature <+8° C. The reaction mixture was stirred with ice bath cooling for 1 hour at which point the reaction was complete by TLC analysis (silica gel, 93:6:1 DCM/MeOH/NH4OH and 6/3/1 CHCl3/MeOH/NH4OH; KMnO4 stain). Additional triethylamine (25.5 mL, 182.5 mmol, 1.10 equiv) was added to the reaction mixture and methanesulfonyl chloride (14.9 mL, 191 mol, 1.15 equiv) was added drop-wise over 45 minutes while maintaining an internal temperature <+10° C. The resulting reaction mixture was stirred with ice bath cooling for about 1.0 hour after which time TLC analysis indicated the reaction was complete. Potassium hydroxide solution (3 M, 220 mL, 650 mmol, 4.0 equiv) was slowly added to the stirred reaction mixture while maintaining an internal temperature <+16° C. The reaction was continued with agitation for 6 hours, after which time the aqueous layer was separated and discarded. Saturated NaHCO3 solution (35 mL) was added and the biphasic mixture heated to 40-42° C. Distillation was started and a first fraction of 90 mL of dichloromethane was collected. When the temperature reached 50° C., a second fraction was collected until the batch temperature was 65° C. The mixture was heated at 65° C. for another 1 hour and then cooled to ambient temperature. Dichloromethane (90 mL)

was added and the mixture stirred for 10 minutes before separation. The dichloromethane layer was concentrated under reduced pressure. The residue was dissolved in heptanes (15 mL) and concentrated under reduced pressure to remove the residual water. This azeotropic drying was repeated two more times. The resulting 4a was obtained as a light-yellow liquid (20.9 g, 76% yield, 95.40% GC purity). A colorless sample was prepared by short path distillation (80-85° C. @ 15 mm Hg vacuum). Optical rotation c=1.00, ethanol, 25.0° C., −38.5°. 1H NMR (300 MHz, CDCl3) δ 3.80 (s, 3H), 3.76 (s, 3H), 2.65-2.50 (m, 1H), 2.42-2.31 (m, 1H), 1.92 (dt, J=3.6, 1.2 Hz, 1H), 1.28 (dd, J=5.4, 1.2 Hz, 3H).

Preparation of 4b:

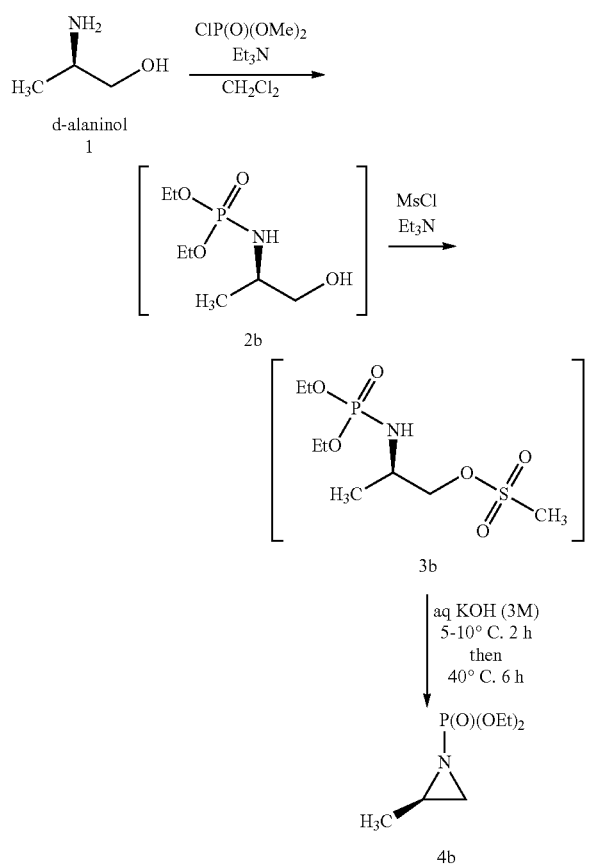

ing an internal temperature <+16° C. The reaction was stirred for 12 hours, after which time the aqueous layer was separated. Sodium chloride (80 g) was added to the aqueous phase and the resulting aqueous phase was extracted with additional dichloromethane (800 mL). The combined organic layers were concentrated under reduced pressure. The resulting R-diethyl (2-methylaziridin-1-yl)phosphonate, 4b, was obtained as a light-yellow liquid (205 g, 80.0% yield, 98.70% GC AUC purity). A colorless sample was prepared by short path distillation at 66-67° C., 0.9 mm Hg. Optical rotation (c=1.148 in EtOH) @ 24.3° C.-28.74°. 1H NMR (300 MHz, CDCl3) δ 4.15 (dq, J=8.0, 7.1 Hz, 4H), 2.64-2.45 (m, 1H), 2.33 (ddd, J=17.9, 5.9, 1.3 Hz, 1H), 1.91-1.81 (m, 1H), 1.34 (dt, J=7.1, 0.9 Hz, 6H), 1.28 (dd, J=5.4, 1.4 Hz, 3H).

Alternate Preparation of 4b:

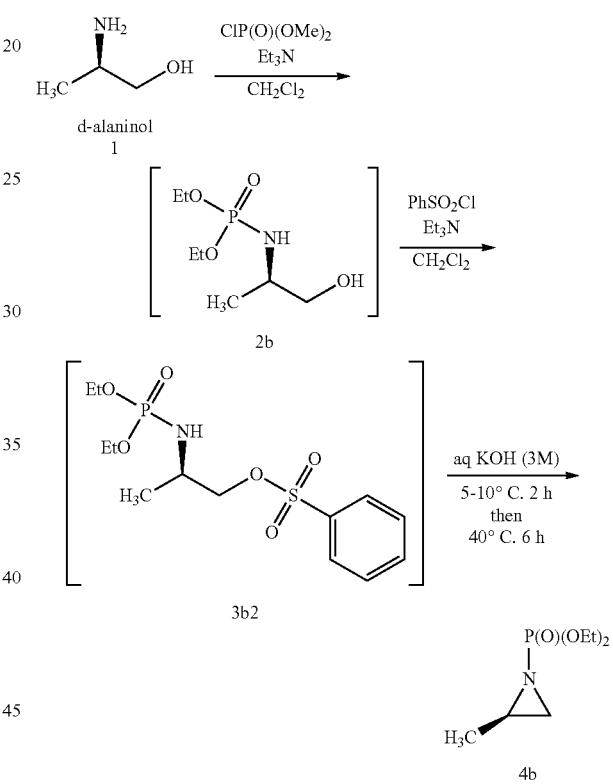

A 5 L 3-neck flask fitted with an overhead mechanical stirrer and 1 L pressure equalizing addition funnel was charged with 1 (d-alaninol, 100.0 g, 1.32 mol), triethylamine (148 g, 1.46 mol, 1.09 equiv) and dichloromethane (2.25 L). The stirred solution was cooled to 0° C. in an acetone/crushed ice/salt bath and diethoxyphosphoryl chloride (229.7 g, 1.32 mol, 1.0 equiv) was added over one hour while maintaining an internal temperature <+5° C. The reaction mixture was stirred an additional 1 hour at which point additional triethylamine (148 g, 1.46 mol, 1.10 equiv) was added to the reaction mixture and methanesulfonyl chloride (152.5 g, 1.32 mol, 1.0 equiv) was added drop-wise over one hours while maintaining an internal temperature <+10° C. The resulting reaction mixture was stirred for 4 hours. An aqueous potassium hydroxide solution (373 g, 6.67 mol, 5 equiv dissolved in 1 L of deionized water) was slowly added to the stirred reaction mixture while maintain- A suitably sized, 3-neck flask equipped with an overhead mechanical stirrer and pressure equalizing addition funnel is charged with 1 (d-alaninol, 12.5 g, 166.4 mmol), triethylamine (29 mL, 208 mmol, 1.25 equiv) and dichloromethane (125 mL). The reaction solution is cooled to 0° C. and then treated with diethoxyphosphoryl chloride (28.7 g, 24 mL, 183 mmol, 1.10 equiv) over 40 minutes while maintaining an internal temperature <+8° C. The reaction mixture is stirred in an ice bath cooling for 1 hour at which point the reaction should be complete by TLC analysis (silica gel, 93:6:1 DCM/MeOH/NH4OH and 6/3/1 CHCl3/MeOH/NH4OH; KMnO4 stain). Additional triethylamine (25.5 mL, 182.5 mmol, 1.10 equiv) is added to the reaction mixture and benzenesulfonyl chloride (33.7 g, 24.4 mL, 191 mol, 1.15 equiv) is added drop-wise over 45 minutes while maintaining an internal temperature <+10° C. The resulting reaction mixture is stirred with ice bath cooling for at least 3.0 hours, until the TLC analysis indicates the reaction was complete.

Potassium hydroxide solution (3 M, 220 mL, 650 mmol, 4.0 equiv) is slowly added to the stirred reaction mixture while maintaining an internal temperature <+20° C. The reaction is stirred overnight at room temperature, after which time the aqueous layer is separated and discarded. The dichloromethane layer is dried over anhydrous magnesium sulfate, clarified and concentrated under reduced pressure. The residue is dissolved in heptanes (15 mL) and concentrated under reduced pressure to remove the residual methylene chloride. The resulting 4b should be obtained as a light-yellow liquid. A colorless sample can be prepared by short path distillation at about 66-67° C. @ 0.9 mm Hg vacuum.

Alternate Preparation of 4b:

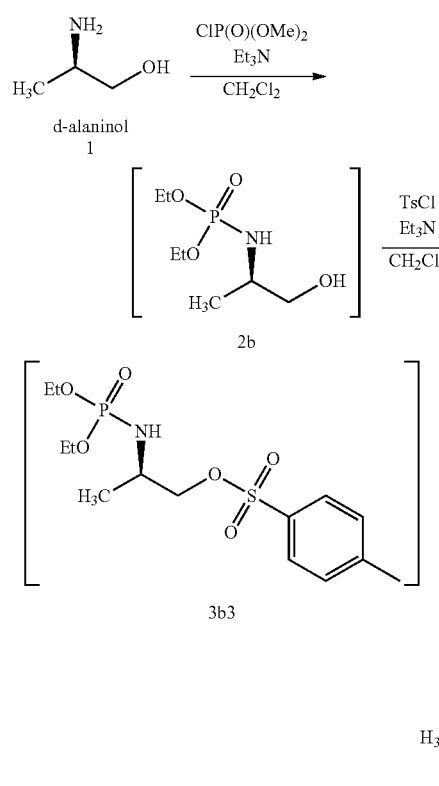

maintaining an internal temperature <+20° C. The reaction is stirred overnight at room temperature, after which time the aqueous layer is separated and discarded. The dichloromethane layer is dried over anhydrous magnesium sulfate, clarified and concentrated under reduced pressure. The residue is dissolved in heptanes (15 mL) and concentrated under reduced pressure to remove the residual methylene chloride. The resulting 4b should be obtained as a light-yellow liquid. A colorless sample can be prepared by short path distillation at about 66-67° C. @ 0.9 mm Hg vacuum.

Preparation of 4c:

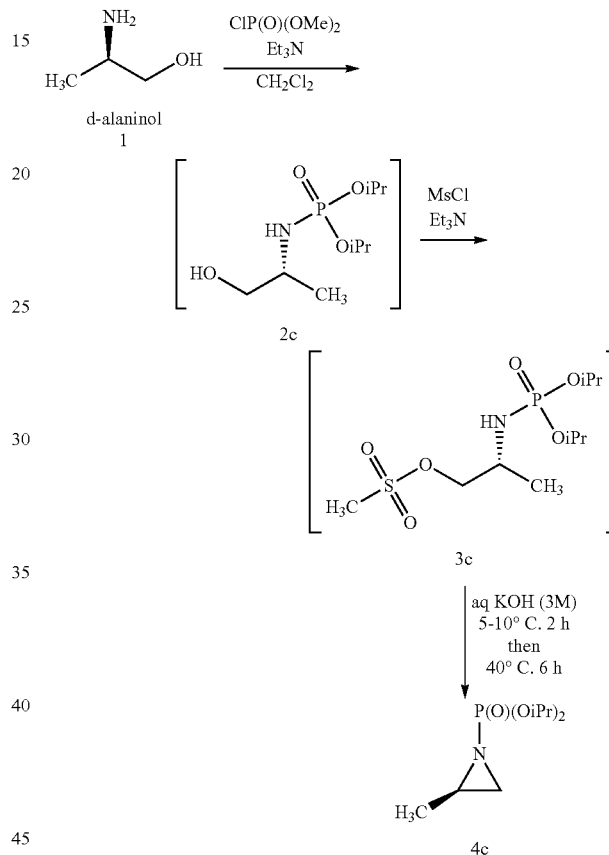

A suitably sized, 3-neck flask equipped with an overhead mechanical stirrer and pressure equalizing addition funnel is charged with 1 (d-alaninol; 12.5 g, 166.4 mmol), triethylamine (29 mL, 208 mmol, 1.25 equiv) and dichloromethane (125 mL). The reaction solution is cooled to 0° C. and then treated with diethoxyphosphoryl chloride (28.7 g, 24 mL, 183 mmol, 1.10 equiv) over 40 minutes while maintaining an internal temperature <+8° C. The reaction mixture is stirred in an ice bath cooling for 1 hour at which point the reaction should be complete by TLC analysis (silica gel, 93:6:1 DCM/MeOH/NH4OH and 6/3/1 CHCl3/MeOH/NH4OH; KMnO4 stain). Additional triethylamine (25.5 mL, 182.5 mmol, 1.10 equiv) is added to the reaction mixture and a solution of p-toluenesulfonyl chloride (TsCl; 36.3 g, 191 mol, 1.15 equiv) in dichloromethane (50 mL) is added drop-wise over 45 minutes, while maintaining an internal temperature <+15° C. The resulting reaction mixture is stirred with ice bath cooling for at least 3.0 hour, until the TLC analysis indicates the reaction was complete. Potassium hydroxide solution (3 M, 220 mL, 650 mmol, 4.0 equiv) is slowly added to the stirred reaction mixture while A 250 L, 3-neck flask fitted with an overhead mechanical stirrer and pressure equalizing addition funnel was charged with 1 (d-alaninol; 4.2 g, 55.7 mmol), triethylamine (9.74 mL, 69.68 mmol, 1.25 equiv) and dichloromethane (50 mL). The stirred reaction solution was cooled to +2° C. and diisopropylphosphoryl chloride (12.3 g, 61.3 mmol, 1.10 equiv) was added drop-wise over 1.3 hours maintaining an internal temperature <+8° C. The reaction mixture was stirred at about 0° C. for 10 hours. Additional triethylamine (8.6 mL, 61.3 mmol, 1.10 equiv) was added to the reaction mixture and methanesulfonyl chloride (4.96 mL, 64.1 mmol, 1.15 equiv) was added over 1.5 hours maintaining an internal temperature <+10° C. The resulting reaction mixture was stirred at about 0° C. for 1.5 hours after which time TLC analysis (see above) indicated the reaction was complete. Potassium hydroxide solution (3 M solution, 74 mL, 222.9 mmol, 4.0 equiv) was slowly added to the stirred reaction mixture while maintaining an internal temperature <+16° C. The reaction was continued with agitation for 6 hours, after which time the layers were separated. The organic layer was washed with 10% citric acid solution (40 mL) and saturated salt solution (2×40 mL). The organic layer was concentrated under reduced pressure and the residue was distilled (bulb-to-bulb; 79-82° C. @ 3 mm Hg vacuum) to afford 4c as a clear colorless liquid (5.2 g, 42.0% yield, 97.0% GC AUC purity). Optical rotation c=1.01, ethanol, 22.5° C., −27.8°. 1H NMR (300 MHz, CDCl3) δ 4.71 (m, 2H), 2.64-2.41 (m, 1H), 2.28 (ddd, J=17.6, 5.6, 1.3 Hz, 1H), 1.81 (dd, J=14.1, 4.9, 1.3 Hz, 1H), 1.34 (m, 12H), 1.22 (dd, J=5.6, 1.2 Hz, 3H).

Preparation of 4d:

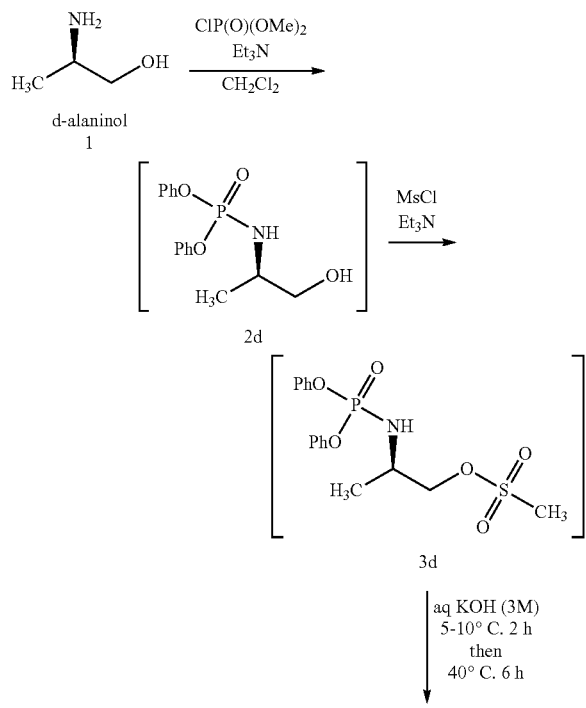

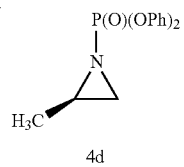

A 500 L 3-neck flask fitted with an overhead mechanical stirrer and a pressure equalizing addition funnel was charged 1 (d-alaninol; 25 g, 332 mmol), triethylamine (57.3 mL, 409.7 mmol, 1.25 equiv) and dichloromethane (500 mL). The stirred reaction mixture was cooled to +2° C. and treated with diphenylphosphoryl chloride (98.2 g, 365.4 mmol, 1.10 equiv) over 1 hour while maintaining an internal temperature <+10° C. The reaction mixture was stirred for 10 hours. Additional triethylamine (51.5 mL, 361.6 mmol, 1.10 equiv) was added to the reaction mixture and methanesulfonyl chloride (29.5 mL, 379.6 mmol, 1.15 equiv) was added over 1 hour while maintaining an internal temperature <+10° C. The resulting reaction mixture was stirred with ice bath cooling for 1.5 hours after which time TLC analysis (see above method) indicated the reaction was complete. Potassium carbonate (180.8 g, 1.31 mol, 4.0 equiv) was added to the cooled, stirred reaction mixture while maintaining an internal temperature <+16° C. The reaction mixture was stirred for 6 hours at ambient temperature. The solid was filtered and the organic phase was washed with 10% citric acid solution (200 mL) and saturated sodium chloride solution (2×150 mL). The organic solution was concentrated under reduced pressure and the residue was purified by column chromatography. The resulting 4d was obtained as viscous oil (57.5 g, 60.0% yield, 96.8% GC purity). Optical rotation c=1.00, ethanol, 25.1° C., −35.2°. 1H NMR (300 MHz, CDCl3) δ 4.71 (m, 2H), 2.64-2.41 (m, 1H), 2.28 (ddd, J=17.6, 5.6, 1.3 Hz, 1H), 1.81 (dd, J=14.1, 4.9, 1.3 Hz, 1H), 1.34 (m, 12H), 1.22 (dd, J=5.6, 1.2 Hz, 3H).

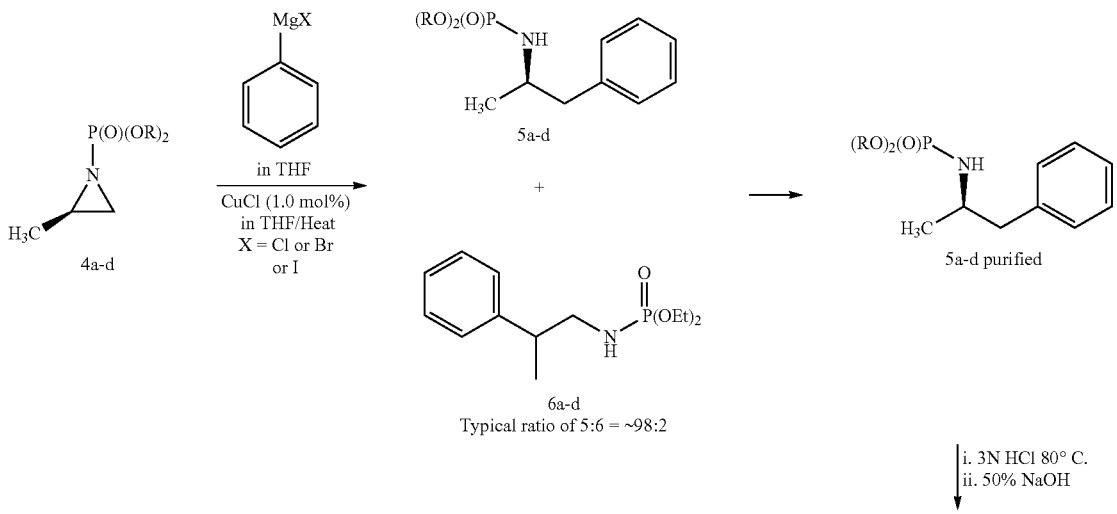

Scheme 2: Preparation of Levoamphetamine Sulfate (8)

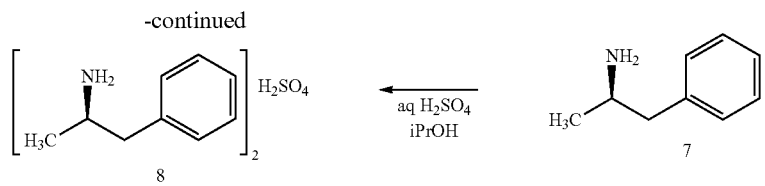

Barbier Preparation of 5b Purified:

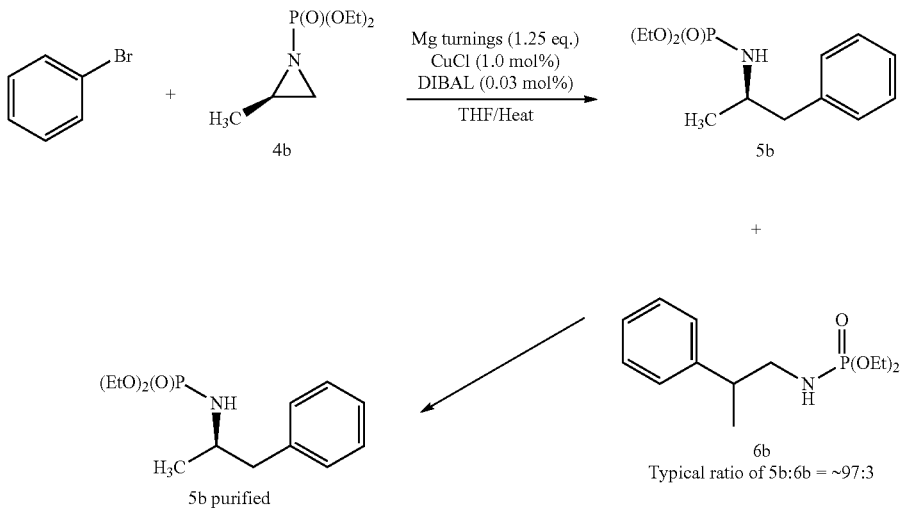

Typical ratio of 5b:6b = ~97:3

A 12 L 4-neck flask with an overhead stirrer, water-cooled condenser, pressure equalizing addition funnel and thermometer was charged with magnesium turnings (31.45 g, 1.3 mol), CuCl (1.18 g, 0.012 mol), 4b (200 g, 1.04 mol) and THF (3900L). The stirrer was started and the mixture was heated to about 40° C. at which point the DIBAL solution (3.4 mL of a 1.0 M solution in THF) was added in one portion. The temperature was increased to 55° C. An initiator portion of bromobenzene (14.8 g; 10 mL) was added in one portion and the reaction stirred for 0.5 hours. The temperature was increased to 60° C. at which point the remaining bromobenzene (172.2 g, 115 mL; 1.20 mol total) in THF (100 mL) was added dropwise over 1.0 hour while maintaining a gentle reflux. The reflux was continued for 2 hours and then the reaction was cooled to ambient temperature. The reaction was quenched by slow addition of ethyl acetate (200 mL). The reaction was then quenched into a cooled (about 15° C.) solution of saturated aqueous ammonium chloride/water (50/50 v/v, 1400 mL) while maintaining an internal temperature below 20° C. Heptanes (1000 mL) was used to rinse the reactor and was transferred to the quench mixture, the mixture was agitated for 5 minutes, allowed to separate for 20 minutes then the aqueous phase was removed. The organic phase washed with deionized water (1000 mL) and the organic phase concentrated under reduced pressure to a volume of about 1.0 L. Heptanes (1.0 L) was added and the solution was concentrated under reduced pressure distillation to a total volume of about 1.0 L. The solution was slowly stirred for 24 hours at ambient temperature to afford a white slurry which was then cooled to 5° C. for about 1.5 hours. The resulting crystalline solid was collected by filtration and washed with cold heptanes (2×250 mL). After drying under vacuum at 35° C. for 48 h, 5b was obtained as a white crystalline solid (220 g, 80.0% yield) 99.8% GC purity (with 0.09% of 6b). mp 64-65° C. Optical rotation c=1.00, ethanol, 25.0° C., −27.7°. 1H NMR (300 MHz, CDCl3) δ 7.32-7.17 (m, 5H), 3.66 (d, J=6.4 Hz, 3H), 3.50-3.83 (m, 1H), 2.71 (d, J=6.6 Hz, 2H), 2.45 (m, 1H), 1.15 (d, J=6.6 Hz, 3H). Chiral analysis (chiral method 2) showed none of the S isomer of 5b was present.

Preparation of 5b purified with prepared phenylmagnesium bromide:

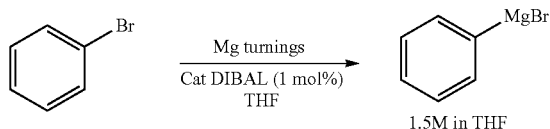

-continued

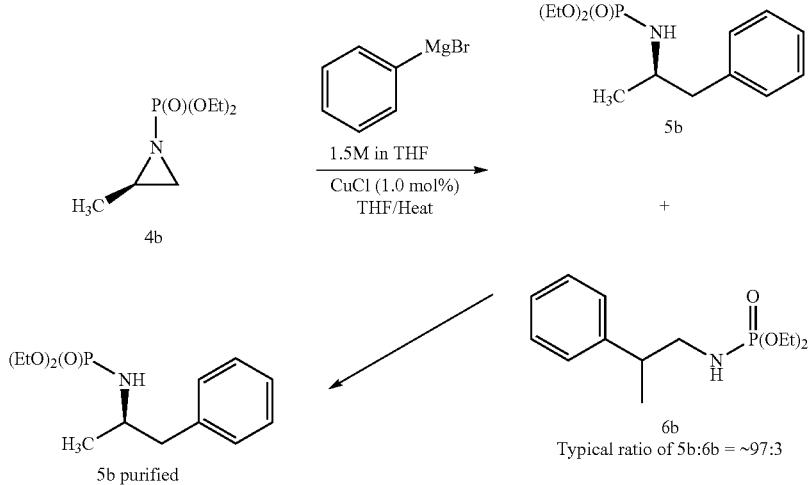

Pt. 1: Grignard Formation:

A 2 L, 3-neck flask with an overhead stirrer, water-cooled condenser, pressure equalizing addition funnel and thermocouple was charged with magnesium turnings (14.2 g, 0.41 mol) and dry THF (400 mL). The stirrer was started and the suspension was heated to 46° C. A catalytic amount of DIBAL solution (2.0 mL of 1.0 M solution in THF) and the suspension was heated to 50° C. Bromobenzene (8.95 g, 6.0 mL) was added in one portion and the reaction initiated within 5 minutes. The batch temperature was raised to 60° C. When the reaction slowed, the balance of the bromobenzene (75.0 g; 100 mL) in THF (175 mL) was added at a steady rate over 1 hour, and the addition funnel rinsed into the batch with fresh THF (50 mL). The maximum batch temperature reached during the addition was 69° C. The reaction was heated to 65° C. and held there for 90 minutes and cooled to 30° C.

Pt 2. Cuprate Reaction

To a 5 L 3-neck flask with an overhead stirrer, water-cooled condenser, pressure equalizing addition funnel and thermocouple was charged with CuCl (320 mg, 1.0 mol %), diethyl(2-methylaziridin-1-yl)phosphonate 4b (80 g, 0.414 mol) and THF (400 mL). The stirrer was started and the mixture was heated to about 45° C. at which point the Grignard solution from part 1 was added over 1.5 hours, while maintaining the internal batch temperature of 48-52° C. Following the Grignard addition, the batch was heated at about 50° C. for an additional hour at which point the batch was cooled to ambient temperature. The reaction was first quenched by slow addition of ethyl acetate (25 mL). The reaction was then cooled to about 15° C. and a solution of saturated aqueous ammonium chloride/water (50/50 v/v, 560 mL) was added while maintaining an internal temperature below 20° C. Heptanes (320 mL) were added to the quenched reaction mixture. The biphasic mixture was mixed for about 30 minutes and allowed to separate overnight at ambient temperature. The layers were separated and the aqueous phase was removed (Note: any remaining rag layer can be broken/removed by an in-line filtration). The organic phase washed with deionized water (75 mL) and the organic phase concentrated under reduced pressure to a volume of about 200 mL. Heptanes (2×80 mL) was added and the solution was concentrated under reduced pressure distillation to a total volume of about 200 mL. The solution was slowly stirred for 24 hours at ambient temperature to afford a white slurry which was then cooled to 5° C. for about 2 hours. The resulting crystalline solid was collected by filtration and washed with cold heptanes (50 mL). The filter cake was air dried for 1 hour and then transferred to a glass drying tray and dried under vacuum at 35° C. for 48 h. Compound 5b was obtained as a white crystalline solid in 61% yield (68.2 g) with 98.8% GC AUC purity (0.16% 6b). GC analysis of dried 5b for residual benzene indicated <1 ppm. The combined mother/wash liquors were concentrated under reduced pressure to about 50 mL to afford a second crop of 5b as a white crystalline solid in 13.4% yield (15.4 g) with 99.5% GC AUC purity (0.09% 6b). GC analysis of dried CAP-0127 second crop, for residual benzene indicated <1 ppm.

1H NMR (300 MHz, CDCl3) δ 7.36-7.08 (m, 5H), 4.14-3.85 (m, 3H), 3.85-3.66 (m, 1H), 3.58-3.32 (m, 1H), 2.81-2.61 (m, 2H), 2.38 (t, J=9.8 Hz, 1H), 1.38-1.18 (m, 6H), 1.15 (d, J=6.4 Hz, 3H).

13C (75.5 MHz, CDCl3) δ 138.7, 129.9, 128.7, 126.7, 62.5 (d, 2JCP=5.4 Hz), 62.4 (d, 2JCP=5.6 Hz), 49.5, 45.5 (d, 2JCP=6.4 Hz), 23.1 (d, 3JCP=4.1 Hz), 16.6 (d, 3JCP=7.3 Hz).

Melting point: 64-66° C.
Optical rotation c=1.10, ethanol, 22.5° C., −27.9.
Preparation of 5b Purified:

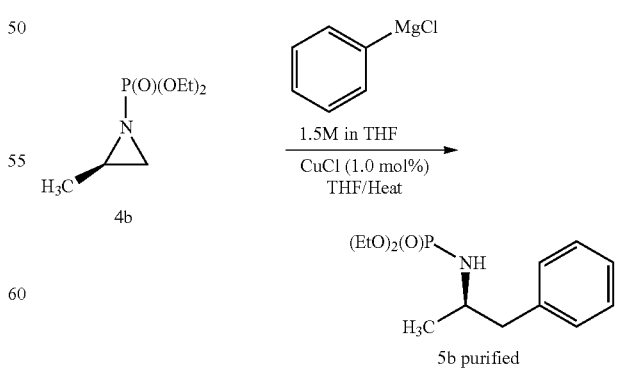

A 12 L, jacketed, bottom outlet flask was charged with 4b (500 g, 2.58 mol), THF (2.5 L) and CuCl (2.0 g, 0.78 mol %) and the stirred mixture was heated to 46° C. A pressure equalizing addition funnel was charged with PhMgCl (commercial 2M in THF, 1.6 L) and the solution was added slowly while maintaining an internal temperature between 48-51° C. After the addition was complete, the reaction mixture was stirred at 48-51° C. for an additional 30 minutes and then cooled to ambient temperature. The reaction was quenched by slow addition to a cooled mixture of saturated aqueous ammonium chloride solution and water (50/50 v/v, 3.0 L) while maintaining an internal temperature below 20° C. The flask was rinsed with heptanes (2.0 L) and the rinse was transferred to the quenched reaction mixture. The biphasic mixture was stirred for 15 min, allowed to separate for 20 min and then the aqueous phase was removed. The organic phase washed with deionized water (500 mL) and the organic phase concentrated under vacuum to a volume of about 1.0 L. Heptanes (1000 mL) was added and the solution volume was adjusted by reduced pressure distillation to a total volume of about 1.5 L. The stirrer was slowed and the crystallization was allowed to proceed for about 24 hours. The slurry was cooled to 5° C. for about 1.5 hours. The resulting crystalline solid was collected by vacuum filtration and washed with cold heptanes (2×200 mL). After drying under vacuum at 35° C. for 48 hours the 5b purified was obtained as a white crystalline solid (565.0 g, 80.5% yield; 99.66% GC purity with 0.04% 6b present). mp 64-65° C. Optical rotation c=1.10, ethanol, 22.5° C., −27.5°. 1H NMR (300 MHz, CDCl3) δ 7.36-7.08 (m, 5H), 4.14-3.85 (m, 3H), 3.85-3.66 (m, 1H), 3.58-3.32 (m, 1H), 2.81-2.61 (m, 2H), 2.38 (t, J=9.8 Hz, 1H), 1.38-1.18 (m, 6H), 1.15 (d, J=6.4 Hz, 3H).

Recrystallization of 5b Purified:

To a 2 L, 3-neck round bottomed flask, equipped with a mechanical stirrer, water-cooled reflux condenser and thermocouple was added 250.0 g of 5b. Heptanes (500 ml) were added, stirring was initiated and the thermocouple was set at 45° C. Upon reaching 45° C., the suspension was noticeably thinner and the color had become somewhat pale yellow. The thermocouple was reset to 60° C. At about 50° C., the suspension quickly gave way to a clear, pale, yellow-brown solution. This solution was heated at about 60° C. for about 90 minutes whereupon the heat was removed and the reaction allowed to cool to ambient temperature. The 5b began crystallizing at 48-50° C. and the batch temperature held at about this temperature during the crystallization. The crystalized batch was stirred at room temperature overnight and cooled in an ice/water bath to about 5° C. The solid 5b was collected by vacuum filtration, air dried, then dried overnight under full vacuum at 35° C. to afford a 94% recovery of 5b Purified (235 g).

Preparation of Levoamphetamine (7):

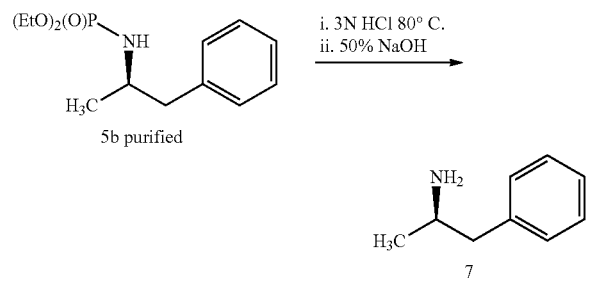

A 2 L jacketed bottom outlet valve flask was charged with 5b purified (300 g, 1.10 mol) and 3 M HCl (725 mL) and the reaction mixture was heated to 80° C. for 1.5 h, then cooled to room temperature. The orange solution was extracted with toluene (500 mL) and the organic extract was discarded. Sodium hydroxide solution (50%, 250 mL) was slowly added to the remaining aqueous layer, bringing the pH up to at least 13. During the pH adjustment keep the internal batch temperature below 25° C. Methyl tert-butyl ether (350 mL) was added and the reaction mixture was agitated for 20 min then allowed to separate for 30 min. The aqueous layer was removed and the organic layer washed with water (250 mL) and concentrated under vacuum to afford a light brown oil. The residue was distilled (Distillation conditions: short path still; head T=65-90° C. (after removal of lower boiling solvent and water), vacuum=4-5 mmHg) to give 7, as a clear colorless oil (125.1 g, 84.1% yield, >99.8% pure by GC). Chiral HPLC analysis (chiral method 1): 99.78% levoamphetamine; 0.22% dextroamphetamine; 99.67% ee.

1H NMR (300 MHz, CDCl3) δ 7.36-7.26 (m, 2H), 7.23-7.13 (m, 3H), 3.26-3.03 (m, 1H), 2.72 (dd, J=13.2, 5.4 Hz, 1H), 2.53 (dd, J=13.2, 8.0 Hz, 1H), 1.20 (br s, 2H), 1.13 (d, J=6.3 Hz, 3H).

13C (75.5 MHz, CDCl3) δ140.2, 129.6, 129.4, 128.9, 128.8, 126.5, 48.9, 47.2, 24.0.

Chiral HPLC analysis retention times: levoamphetamine 14.3 min, dextroamphetamine 16.1 min Optical rotation c=2.0, methanol, 22° C., −29.2°.

Preparation of Levoamphetamine Sulfate (8):

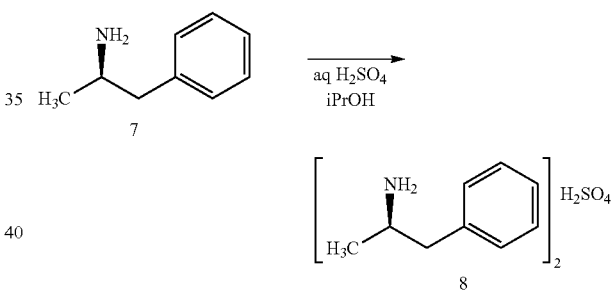

To a chilled mixture of water (70 mL) and isopropanol (145 mL) in a 1 L Erlenmeyer flask was slowly added concentrated sulfuric acid (40.4 g; 22 mL; 0.41 mol). To a 5 L, 3-necked round bottomed flask equipped with a temperature probe, inert gas purge, pressure equalized addition funnel was charged 7 (110.0 g; 0.814 mol), water (40 mL) and isopropanol (700 mL) and the stirrer was started. The isopropanol-aqueous sulfuric acid mixture was added at a rate to keep the batch temperature below 45° C. The acid solution was rinsed in with additional isopropanol (175 mL). During the addition, the solid product started to crystalize. After the addition was complete, the batch temperature was increased to reflux (81° C.). Additional water (265 mL) was added in portions (260 mL) to achieve a complete solution. The heat was removed and the batch was allowed to cool. The 8 began to crystallize at 65° C. and the stirred batch was cooled to 25° C. overnight. The following morning, the batch was cooled to 5° C. and stirred for 2 hours. The solids were collected by vacuum filtration and the flask and filter cake was rinsed with cold isopropanol (100 mL). The solids were vacuum dried at 35-40° C. for 48 hours to afford 8 (124.0 g; 93.2% yield) as a white crystalline solid.

Preparation of 5a Purified:

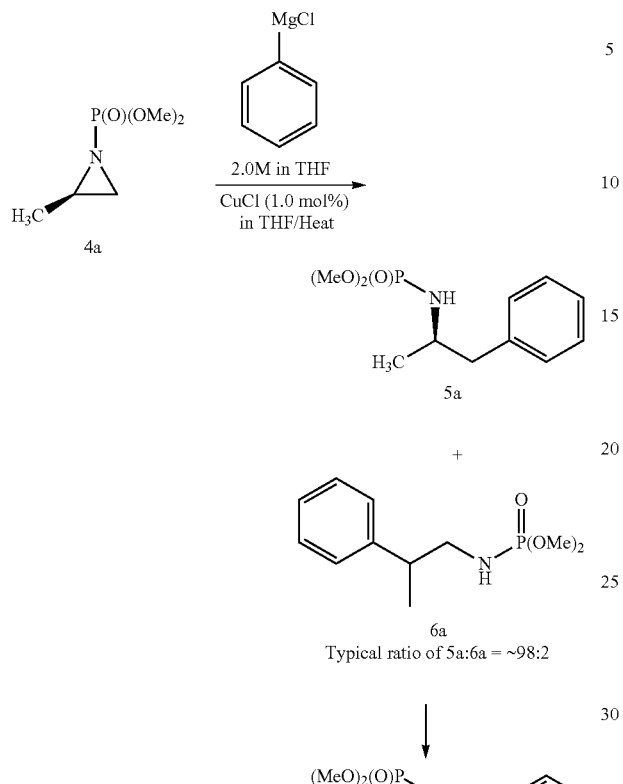

A 100 mL 3-neck flask was charged with 4a (4.0 g, 24.2 mmol), THF (25 mL) and CuCl (28 mg, 1 mol %) and the stirrer was started. The mixture was heated to 48° C. A pressure equalizing addition funnel was charged with PhMgCl (2M in THF, 13 mL) and the solution was added slowly while maintaining an internal temperature between 48-51° C. The reaction was stirred at 48-51° C. for an additional 30 minutes and then cooled to ambient temperature. The reaction was quenched by slow addition to a cooled (15° C.) solution of saturated aqueous ammonium chloride in water (50/50 v/v, 40 mL) while maintaining the temperature below 20° C. Heptanes (40 mL) was used to rinse the reactor and the rinse solution was transferred to the quenched reaction mixture. The mixture was agitated for 5 minutes, allowed to separate for 20 minutes then the aqueous phase was discarded. The organic phase washed with deionized water (10 mL) and the organic phase concentrated under reduced pressure to give an oil. The residue was dissolved in heptanes (50 mL) and the solution was concentrated under reduced pressure. The residue was crystallized from methyl tert-butyl ether (1 g/3 mL), filtered and dried to give 5a purified as white needles (3.29 g; 60.2% yield), with 99.89% GC purity (containing 0.05% 6a). mp 86-88° C. Optical rotation c=1.00, ethanol, 25.0° C., −28.8°. 1H NMR (300 MHz, CDCl3) δ 7.32-7.17 (m, 5H), 3.66 (d, J=6.4 Hz, 3H), 3.50-3.83 (m, 1H), 2.71 (d, J=6.6 Hz, 2H), 2.45 (m, 1H), 1.15 (d, J=6.6 Hz, 3H).

Preparation of Levoamphetamine (7):

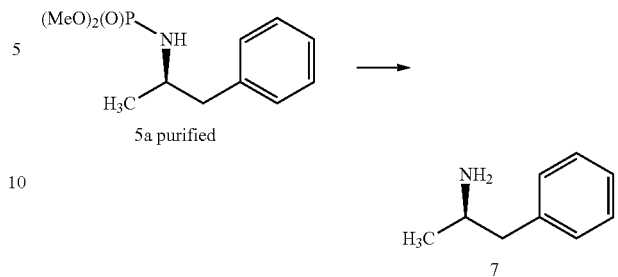

A 50-mL flask was charged with 5a purified (3.0 g, 12.3 mmol) and 3 M HCl (15.0 mL) and the stirred reaction mixture was heated to 80° C. for 1 hour, then cooled to room temperature. The reaction mixture was washed with isopropyl acetate (2×20 mL) and the organic extracts were disposed. The aqueous layer was treated with sodium hydroxide solution (50%, 15.0 mL) keeping the internal temperature below 25° C. Methyl tert-butyl ether (15 mL) was added and the reaction mixture was agitated for 5 minutes then allowed to separate. The organic layer washed with water (10 mL) and concentrated under reduced pressure to give levoamphetamine 7 as a colorless oil (1.57 g, 95% yield, >99.5% purity by GC and chiral HPLC).

Preparation of 5c Purified:

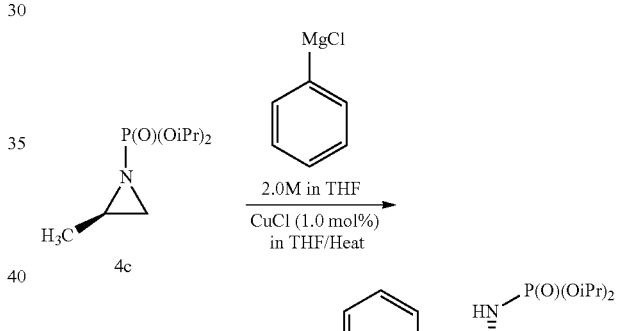

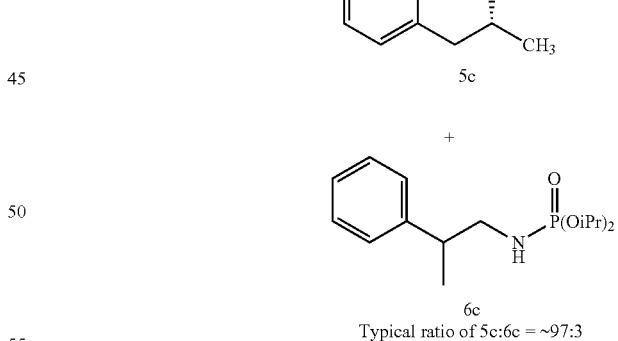

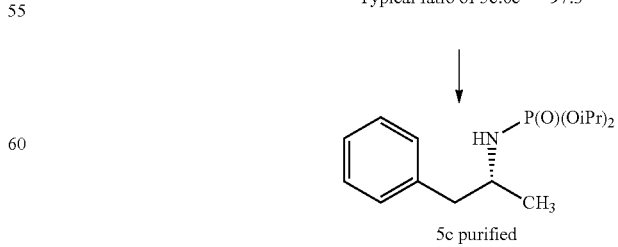

A 100-mL jacketed flask equipped with an overhead stirrer was charged with 4a (5.0 g, 22.6 mmol), THF (25 mL)

and CuCl (23 mg, 1 mol %). The stirrer was started, and the mixture was heated to 48° C. A pressure equalizing addition funnel was charged with PhMgCl (2M in THF, 12.4 mL) and this solution was added while maintaining the internal temperature of 48-51° C. The reaction was allowed to stir at 48-51° C. for 30 minutes after Grignard addition and then cooled to 20° C. The reaction was quenched by slow addition to a pre-cooled (15° C.) solution of saturated aqueous ammonium chloride solution in water (50/50 v/v, 40 mL) while maintaining an internal temperature below 20° C. Heptanes (40 mL) was used to rinse the reactor and the rinse solution was added to the quench mixture. The mixture was agitated for 5 minutes, allowed to separate for 20 minutes and then the aqueous phase was removed. The organic phase washed with deionized water (10 mL) and the organic phase concentrated under reduced pressure. The residue was dissolved in heptanes (50 mL) and the solution was concentrated to dryness under reduced pressure. The residue was purified by chromatography. The appropriate fractions were concentrated to dryness under reduced pressure to give the desired product as a slow crystallizing solid (4.4 g, 65%, 92% GC purity). The GC analysis indicated the presence of 8% biphenyl as well as 0.09% of 6c. A 1 g sample was removed and crystallized from 1 volume cold heptanes at −15° C. The resulting crystals of 5c purified (0.421 mg, 42% recovery) were found to be 99.75% pure by GC analysis with 0.04% of 6c. The crystalline 5c purified melted when the sample reached room temperature. Optical rotation c=1.10, ethanol, 22.5° C., −27.4°. 1H NMR (300 MHz, CDCl3) δ 7.32-7.17 (m, 5H), 4.59-4.41 (m, 2H), 3.53-3.41 (m, 1H), 2.86-2.80 (m, 1H), 2.69-2.61 (m, 1H), 2.36 (t, J=9.6 Hz, 1H), 1.32-1.26 (m, 12H), 1.08 (d, J=10.1 Hz, 3H).

Preparation of Levoamphetamine (7):

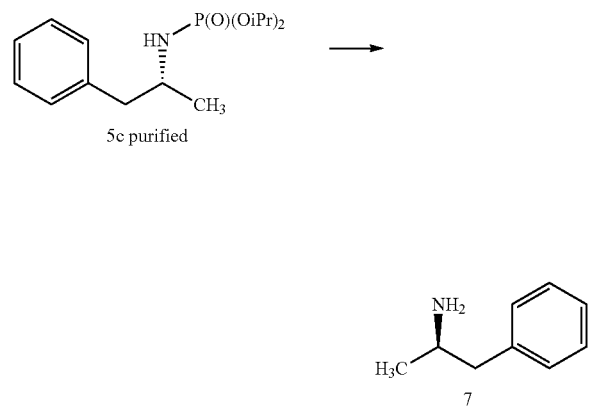

A 50-mL flask was charged with 5c purified (3.0 g, 10 mmol) and 3 M HCl (15 mL) and the stirred reaction mixture was heated to 80° C. for 12 hours, then cooled to room temperature. The aqueous solution was washed with isopropyl acetate (2×20 mL) and the organic extract was discarded. The aqueous layer was treated with sodium hydroxide solution (50%, 10.0 mL) keeping the internal temperature below 25° C. Methyl tert-butyl ether (40 mL) was added and the reaction mixture was agitated for 5 minutes then allowed to separate for 15 minutes. The aqueous layer was extracted with methyl tert-butyl ether (40 mL) and the combined organic layers were washed with water (10 mL) and concentrated under reduced pressure to give 7 as a colorless oil (1.1 g, 82% yield, >98% purity by GC and chiral HPLC).

Preparation of 5d Purified

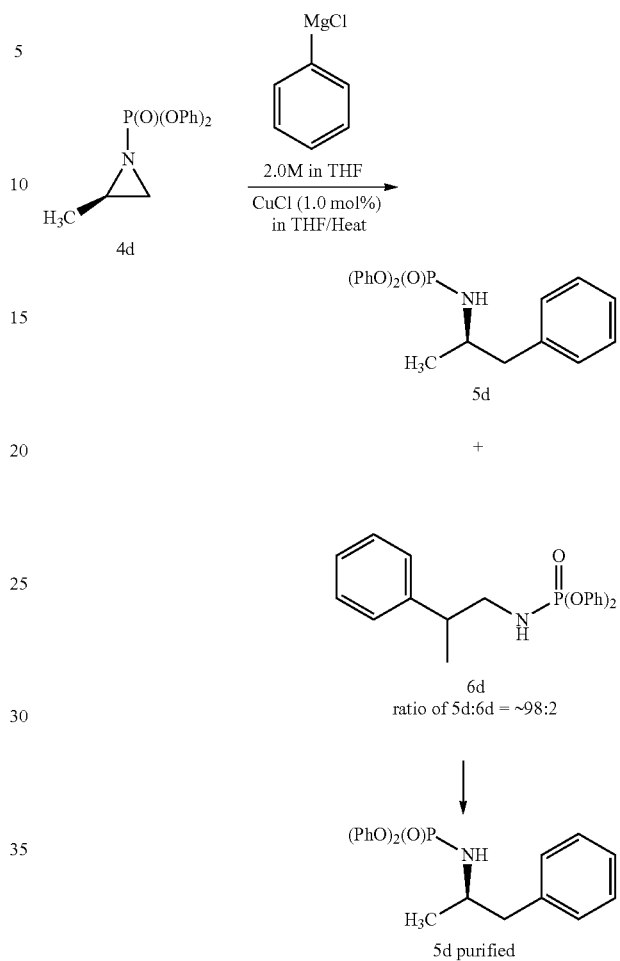

A 500-mL jacketed flask was charged with 4d (10.0 g, 34.6 mmol), THF (100 mL) and CuCl (42 mg, 1 mol %) and the stirred mixture was heated to 48° C. A pressure equalizing addition funnel was charged with PhMgCl (2M in THF, 18 mL) and the solution was added slowly while maintaining a reaction temperature of 48-51° C. The reaction was allowed to stir at 48-51° C. for an additional 30 minutes and then cooled to ambient temperature. The reaction was quenched by slow addition to a cooled (15° C.) solution of saturated aqueous ammonium chloride/water mixture (50/50 v/v, 75 mL) while maintaining the batch temperature below 20° C. Heptanes (100 mL) was used to rinse the reactor and was transferred to the quench mixture. The mixture was agitated for 5 minutes and the aqueous layer was removed. The organic layer washed with deionized water (25 mL) and the organic phase concentrated under reduced pressure to give an oil. This residue was dissolved in heptanes (100 mL) and the solution was concentrated under reduced pressure to afford a gummy solid. The gummy solid was crystallized from ethanol (1 g/5 mL) to give 5d purified as a white solid (7.5 g, 60% yield, 99.65% GC AUC purity). mp 102-103° C. (lit 101-102° C.). Optical rotation c=1.00, methanol, 25.0° C., −18.4°. 1H NMR (300 MHz, CDCl3) δ 7.38-7.11 (m, 15H), 3.83-3.65 (m, 1H), 3.00-2.89 (m, 1H), 2.86-2.78 (m, 1H), 2.73-2.62 (m, 1H), 1.15 (d, J=10.1 Hz, 3H).

Preparation of Levoamphetamine (7):

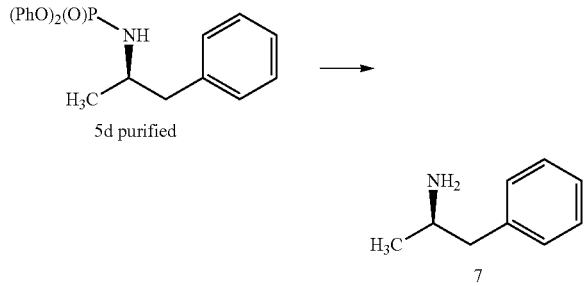

A 50-mL flask was charged with 5d purified (7.24 g, 19.71 mmol) and 3 M HCl (15.0 mL) and the stirred reaction mixture was heated to 80° C. for 32 hours, at which point it was cooled to room temperature. The organic layer was washed with isopropyl acetate (2×20 mL) and the organic extracts were discarded. The aqueous layer was treated with sodium hydroxide solution (50%, 3.0 mL to a pH of 14) keeping the internal temperature below 25° C. Methyl tert-butyl ether (40 mL) was added and the reaction mixture was agitated for 5 minutes and then separated. A second portion of methyl tert-butyl ether (40 mL) was added and the reaction mixture was agitated for 5 minutes. The combined organic extracts were washed with water (10 mL) and concentrated under reduced pressure to give 7 as a colorless oil (2.05 g, 76.9% yield, >99% purity by GC and chiral HPLC).

Examples of Alternate Sulfonates

Preparation of R-diethyl (2-methylaziridin-1-yl)phosphonate (4b):

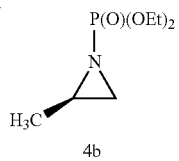

A 5 L 3-neck flask fitted with an overhead mechanical stirrer and 1 L pressure equalizing addition funnel was charged with d-alaninol (1; 100.0 g, 1.32 mol), triethylamine (148 g, 1.46 mol, 1.09 equiv) and dichloromethane (2.25 L). The stirred solution was cooled to 0° C. in an acetone/crushed ice/salt bath and diethoxyphosphoryl chloride (229.7 g, 1.32 mol, 1.0 equiv) was added over one hour while maintaining an internal temperature <+5° C. The reaction mixture was stirred an additional 1 hour at which point additional triethylamine (148 g, 1.46 mol, 1.10 equiv) was added to the reaction mixture and methanesulfonyl chloride (152.5 g, 1.32 mol, 1.0 equiv) was added drop-wise over one hours while maintaining an internal temperature <+10° C. The resulting reaction mixture was stirred for 4 hours. An aqueous potassium hydroxide solution (373 g, 6.67 mol, 5 equiv dissolved in 1 L of deionized water) was slowly added to the stirred reaction mixture while maintaining an internal temperature <+16° C. The reaction was stirred for 12 hours, after which time the aqueous layer was separated. Sodium chloride (80 g) was added to the aqueous phase and the resulting aqueous phase was extracted with additional dichloromethane (800 mL). The combined organic layers were concentrated under reduced pressure. The resulting R-diethyl (2-methylaziridin-1-yl)phosphonate, 4b, was obtained as a light-yellow liquid (205 g, 80.0% yield, 98.70% GC AUC purity). A colorless sample was prepared by short path distillation at 66-67° C., 0.9 mm Hg. Optical rotation (c=1.148 in EtOH) @ 24.3° C.-28.74°. 1H NMR (300 MHz, CDCl3) δ 4.15 (dq, J=8.0, 7.1 Hz, 4H), 2.64-2.45 (m, 1H), 2.33 (ddd, J=17.9, 5.9, 1.3 Hz, 1H), 1.91-1.81 (m, 1H), 1.34 (dt, J=7.1, 0.9 Hz, 6H), 1.28 (dd, J=5.4, 1.4 Hz, 3H).

Alternate Preparation of R-diethyl (2-methylaziridin-1-yl)phosphonate (4b):

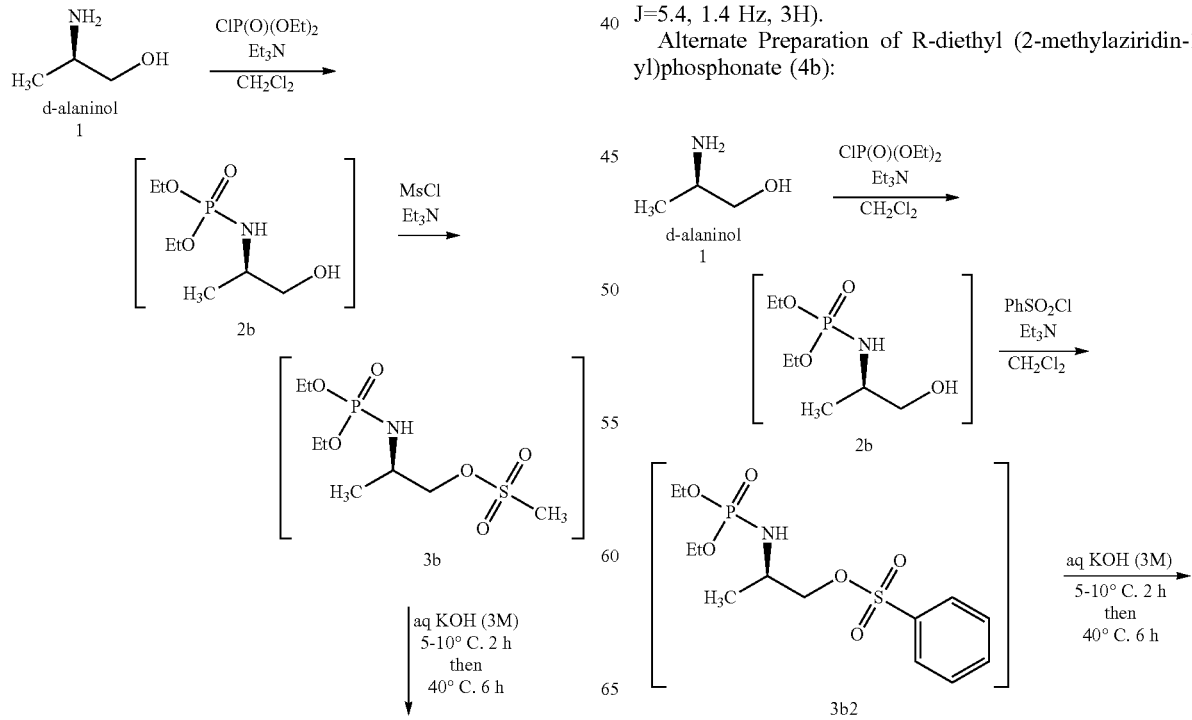

-continued

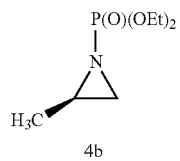

4b

A suitably sized, 3-neck flask equipped with an overhead mechanical stirrer and pressure equalizing addition funnel is charged with d-alaninol (12.5 g, 166.4 mmol), triethylamine (29 mL, 208 mmol, 1.25 equiv) and dichloromethane (125 mL). The reaction solution is cooled to 0° C. and then treated with diethoxyphosphoryl chloride (28.7 g, 24 mL, 183 mmol, 1.10 equiv) over 40 minutes while maintaining an internal temperature <+8° C. The reaction mixture is stirred in an ice bath cooling for 1 hour at which point the reaction should be complete by TLC analysis (silica gel, 93:6:1 DCM/MeOH/NH4OH and 6/3/1 CHCl3/MeOH/NH4OH; KMnO4 stain). Additional triethylamine (25.5 mL, 182.5 mmol, 1.10 equiv) is added to the reaction mixture and benzenesulfonyl chloride (33.7 g, 24.4 mL, 191 mol, 1.15 equiv) is added drop-wise over 45 minutes while maintaining an internal temperature <+10° C. The resulting reaction mixture is stirred with ice bath cooling for at least 3.0 hours, until the TLC analysis indicates the reaction was complete. Potassium hydroxide solution (3 M, 220 mL, 650 mmol, 4.0 equiv) is slowly added to the stirred reaction mixture while maintaining an internal temperature <+20° C. The reaction is stirred overnight at room temperature, after which time the aqueous layer is separated and discarded. The dichloromethane layer is dried over anhydrous magnesium sulfate, clarified and concentrated under reduced pressure. The residue is dissolved in heptanes (15 mL) and concentrated under reduced pressure to remove the residual methylene chloride. The resulting 4b should be obtained as a light-yellow liquid. A colorless sample can be prepared by short path distillation at about 80-85° C. @ 15 mm Hg vacuum.

Alternate Preparation of R-diethyl (2-methylaziridin-1-yl)phosphonate (4b):

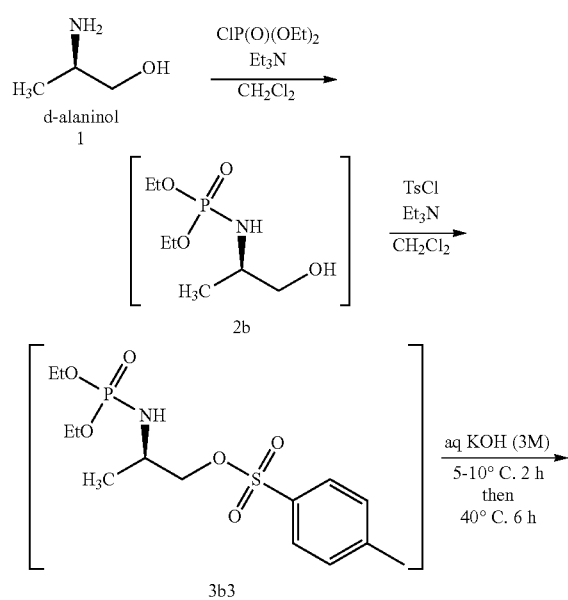

-continued

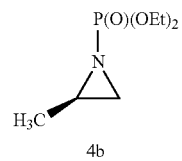

4b

A suitably sized, 3-neck flask equipped with an overhead mechanical stirrer and pressure equalizing addition funnel is charged with d-alaninol (12.5 g, 166.4 mmol), triethylamine (29 mL, 208 mmol, 1.25 equiv) and dichloromethane (125 mL). The reaction solution is cooled to 0° C. and then treated with diethoxyphosphoryl chloride (28.7 g, 24 mL, 183 mmol, 1.10 equiv) over 40 minutes while maintaining an internal temperature <+8° C. The reaction mixture is stirred in an ice bath cooling for 1 hour at which point the reaction should be complete by TLC analysis (silica gel, 93:6:1 DCM/MeOH/NH4OH and 6/3/1 CHCl3/MeOH/NH4OH; KMnO4 stain). Additional triethylamine (25.5 mL, 182.5 mmol, 1.10 equiv) is added to the reaction mixture and a solution of p-toluenesulfonyl chloride (TsCl; 36.3 g, 191 mol, 1.15 equiv) in dichloromethane (50 mL) is added drop-wise over 45 minutes, while maintaining an internal temperature <+15° C. The resulting reaction mixture is stirred with ice bath cooling for at least 3.0 hour, until the TLC analysis indicates the reaction was complete. Potassium hydroxide solution (3 M, 220 mL, 650 mmol, 4.0 equiv) is slowly added to the stirred reaction mixture while maintaining an internal temperature <+20° C. The reaction is stirred overnight at room temperature, after which time the aqueous layer is separated and discarded. The dichloromethane layer is dried over anhydrous magnesium sulfate, clarified and concentrated under reduced pressure. The residue is dissolved in heptanes (15 mL) and concentrated under reduced pressure to remove the residual methylene chloride. The resulting 4b should be obtained as a light-yellow liquid. A colorless sample can be prepared by short path distillation at about 80-85° C. @ 15 mm Hg vacuum.

Amphetamine Assay—Capsules Standard

USP Reference standards 〈11〉—USP Dextroamphetamine Sulfate RS

Identification—

A: Mix an amount of the Capsule contents, equivalent to about 50 mg of dextroamphetamine (sulfate) made according to the process for preparing amphetamines described herein that comprises a cuprate reaction of a phosphoramidate compound in the presence of a Grignard reagent, followed by hydroxide reduction of the alkyl side chain, followed by a first solvent crystallization in THF and heptanes, and a second solvent recrystallization in heptanes, made into a sulfate salt, with about 10 mL of water for 30 minutes, and filter into a small flask. Cool the filtrate to about 15°, add 3 mL of 1 N sodium hydroxide, then add 1 mL of a mixture of 1 volume of benzoyl chloride and 2 volumes of anhydrous ethyl ether, and shake for 2 minutes. Filter the precipitate, wash with about 15 mL of cold water, and recrystallize twice from diluted alcohol: the benzoyl derivative of dextroamphetamine so obtained, after being dried at 105° for 1 hour, melts between 154° and 160°.

B: The retention time of the major peak in the chromatogram of the Assay preparation is the same as that of the Standard preparation obtained in the Assay.

Dissolution, Procedure for a Pooled Sample ⟨711⟩—
Medium: water; 500 mL.
Apparatus 1: 100 rpm.
Time: 45 minutes.
Procedure—Determine the amount of (C9H13N)2·H2SO4 dissolved, employing the procedure set forth in the Assay, making any necessary modifications.

Tolerances—Not less than 75% (Q) of the labeled amount of (C9H13N)2·H2SO4 is dissolved in 45 minutes.

USP 37

Uniformity of dosage units ⟨905⟩: meet the requirements.

Assay—

Mobile Phase—

Dissolve 1.1 g of sodium 1-heptanesulfonate in 525 mL of water. Add 25 mL of dilute glacial acetic acid (14 in 100) and 450 mL of methanol. Adjust dropwise, if necessary, with glacial acetic acid to a pH of 3.3±0.1. Filter through a 0.5-μm membrane filter. The volume of methanol may be adjusted so that the retention time for dextroamphetamine is about 5 minutes.

Standard Preparation—

Dissolve an accurately weighed quantity of USP Dextroamphetamine Sulfate RS, made according to the process for preparing amphetamines described herein that comprises a cuprate reaction of a phosphoramidate compound in the presence of a Grignard reagent, followed by hydroxide reduction of the alkyl side chain, followed by a first solvent crystallization in THF and heptanes, and a second solvent recrystallization in heptanes, made into a sulfate salt, in 0.12 N phosphoric acid to obtain a solution having a known concentration of about 0.3 mg per mL.

Assay Preparation—

Remove, as completely as possible, the contents of not fewer than 20 Capsules, and weigh. Transfer an accurately weighed portion of the mixed powder, equivalent to about 15 mg of dextroamphetamine sulfate as made herein, to a 50-mL volumetric flask. Add 40 mL of 0.12 N phosphoric acid, and sonicate for 15 minutes. Dilute with 0.12 N phosphoric acid to volume, and mix. Filter through a 0.5-μm membrane filter, discarding the first 20 mL of the filtrate.

Chromatographic System

The liquid chromatograph is equipped with a 254-nm detector and a 3.9-mm×30-cm column that contains packing L1. The flow rate is about 2 mL per minute. Chromatograph three replicate injections of the Standard preparation, and record the peak responses as directed for Procedure: the relative standard deviation is not more than 2.0%.

Procedure—

Separately inject equal volumes (about 50 μL) of the Standard preparation and the Assay preparation into the chromatograph by means of a suitable automatic injector or sampling valve, record the chromatograms, and measure the responses for the major peaks. Calculate the quantity, in mg, of (C9H13N)2·H2SO4 in the portion of Capsules taken by the formula:

50C(rU/rS)

in which C is the concentration, in mg per mL, of USP Dex-troamphetamine Sulfate RS in the Standard preparation; and rU and rS are the peak responses obtained from the Assay preparation and the Standard preparation, respectively.

Amphetamine Assay—Tablets

USP Reference standards Tablets ⟨11⟩—USP Dextroamphetamine Sulfate RS

Identification—

A: Transfer a portion of finely ground Tablets, equivalent to about 50 mg of dextroamphetamine (sulfate) made according to the process for preparing amphetamines described herein that comprises a cuprate reaction of a phosphoramidate compound in the presence of a Grignard reagent, followed by hydroxide reduction of the alkyl side chain, followed by a first solvent crystallization in THF and heptanes, and a second solvent recrystallization in heptanes, made into a sulfate salt, to a suitable centrifuge tube. Add 25 mL of water, shake vigorously, and centrifuge until clear. Decant the clear solution into a 250-mL separator, add 5 mL of 2.5 N sodium hydroxide, mix, and extract with 60 mL of ether. Wash the ether extract with two 5-mL portions of 0.25 N sodium hydroxide, and discard the washings. Filter the ether extract through a pledget of cotton, previously saturated with ether, into a 100-mL beaker, and evaporate on a steam bath in a current of air to about 1 mL. Dissolve the residue in 3 mL of alcohol, and transfer to a glass-stoppered, 125-mL conical flask containing 25 mL of water. Rinse the beaker with 3 mL of alcohol, and transfer to the flask. Cool to about 15°, add 3 mL of 1 N sodium hydroxide, then add 1 mL of a mixture of 1 volume of benzoyl chloride and 2 volumes of anhydrous ethyl ether, and shake for 2 minutes. Filter the precipitate, wash with about 15 mL of cold water, and recrystallize twice from diluted alcohol: the benzoyl derivative of dextro-amphetamine so obtained, after being dried at 105° for 1 hour, melts between 154° and 160°.

B: The retention time of the major peak in the chromatogram of the Assay preparation corresponds to that in the chromatogram of the Standard preparation, as obtained in the Assay.

Dissolution, Procedure for a Pooled Sample—
Medium: water; 500 mL.
Apparatus 1: 100 rpm.
Time: 45 minutes.
Determine the amount of (C9H13N)2·H2SO4 dissolved by employing the following method.

Mobile Phase—

Dissolve 1.1 g of sodium 1-heptanesulfonate in 575 mL of water. Add 25 mL of dilute glacial acetic acid (14 in 100) and 400 mL of methanol. Adjust by the dropwise addition of glacial acetic acid to a pH of 3.3±0.1, if necessary, filter, and degas the solution. Make adjustments if necessary.

Chromatographic System

The liquid chromatograph is equipped with a 210-nm detector and a 3.9-mm×30-cm column that contains packing L1. The flow rate is about 1.5 mL per minute. The column temperature is maintained at 40°. Chromatograph replicate injections of the Standard solution, and record the peak responses as directed for Procedure: the relative standard deviation is not more than 2.0%.

Procedure—

Inject a volume (about 100 μL) of a filtered portion of the solution under test into the chromatograph, record the chromatogram, and measure the response for the major peak. Calculate the quantity of (C9H13N)2·H2SO4 dissolved in comparison with a Standard solution having a known concentration of USP Dextroamphetamine Sulfate RS in the same Medium and similarly chromatographed.

Tolerances—

Not less than 75% (Q) of the labeled amount of (C9H13N)2·H2SO4 is dissolved in 45 minutes.

Isomeric Purity—

Pack a pledget of fine glass wool in the base of a 200-×25-mm chromatographic tube, with the aid of a tamping rod. Add 5 g of chromatographic siliceous earth, and tamp firmly to compress the material to a uniform mass.

Finely powder a number of Tablets, equivalent to about 300 mg of dextroamphetamine (sulfate) made according to the process for preparing amphetamines described herein that comprises a cuprate reaction of a phosphoramidate compound in the presence of a Grignard reagent, followed by hydroxide reduction of the alkyl side chain, followed by a first solvent crystallization in THF and heptanes, and a second solvent recrystallization in heptanes, made into a sulfate salt, mix the powder in a mortar with 5 g of chromatographic siliceous earth, add 1 mL of methanol and 0.5 mL of ammonium hydroxide, and triturate to a uniform mixture. Transfer the mixture without delay to the chromatographic tube, and tamp as before. Wipe the mortar and pestle with a small amount of glass wool, and insert it into the tube on top of the column. Arrange a 125-mL separator containing 35 mL of 0.1 N sulfuric acid to receive the effluent. Pass 60 mL of chloroform through the column. Shake the separator vigorously for 1 minute, allow the layers to separate, and discard the chloroform. Add to the aqueous phase in the separator 2.5 g of sodium bicarbonate, preventing it from coming in contact with the mouth of the separator, swirl until most of the bicarbonate has dissolved. By means of a 1-mL syringe, rapidly inject 1.0 mL of acetic anhydride directly into the contents of the separator. Immediately insert the stopper in the separator, and shake vigorously until the evolution of carbon dioxide has ceased, releasing the pressure as necessary through the stopcock. Allow to stand for 5 minutes, and extract the solution with 50 mL of chloroform, shaking vigorously for 1 minute. Filter the chloroform extract through a pledget of filter cotton into a 100-mL beaker, rinse the cotton with a small amount of chloroform, and evaporate on a steam bath in a current of air or nitrogen to dryness. Heat and triturate the residue until the odor of chloroform is no longer perceptible. Allow the residue to cool, inducing it to crystallize. Reduce the crystals to a fine powder, heat at 80° for 30 minutes, and cool: the specific rotation of the acetyl amphetamine so obtained, determined in a solution in chloroform containing 20 mg per mL, a 200-mm semimicro polarimeter tube being used, is between −37.5° and −44.0°.

Assay—

Mobile Phase—

Dissolve 1.1 g of sodium 1-heptanesulfonate in 525 mL of water. Add 25 mL of dilute glacial acetic acid (14 in 100) and 450 mL of methanol. Adjust dropwise, if necessary, with glacial acetic acid to a pH of 3.3±0.1. Filter through a 0.5-μm membrane filter. Make adjustments if necessary.

Standard Preparation—

Dissolve an accurately weighed quantity of USP Dextroamphetamine Sulfate RS, as made according to the cuprate process herein, in 0.12 N phosphoric acid to obtain a solution having a known concentration of about 0.3 mg per mL.

Assay Preparation—

Weigh and finely powder not fewer than 20 Tablets. Transfer an accurately weighed portion of the mixed powder, equivalent to about 15 mg of dextroamphetamine sulfate, as made according to the cuprate process herein, to a 50-mL volumetric flask. Add 40 mL of 0.12 N phosphoric acid, and sonicate for 15 minutes. Dilute with 0.12 N phosphoric acid to volume, and mix. Filter through a 0.5-μm membrane filter, discarding the first 20 mL of the filtrate.

Chromatographic System

The liquid chromatograph is equipped with a 254-nm detector and a 3.9-mm×30-cm column that contains packing L1. The flow rate is about 2 mL per minute. Chromatograph replicate injections of the Standard preparation, and record the peak responses as directed for Procedure: the tailing factor is not more than 3, and the relative standard deviation is not more than 2.0%.

Procedure—

Separately inject equal volumes (about 50 μL) of the Standard preparation and the Assay preparation into the chromatograph, record the chromatograms, and measure the responses for the major peaks. Calculate the quantity, in mg, of (C9H13N)2·H2SO4 in the portion of Tablets taken by the formula:

50C(rU/rS)

in which C is the concentration, in mg per mL, of USP Dextroamphetamine Sulfate RS in the Standard preparation; and rU and rS are the peak responses obtained from the Assay preparation and the Standard preparation, respectively.

Additional Comparison Step Option

Confirm 98%+ purity of the dextroamphetamine sulfate, as made according to the cuprate process herein.

Then, compare to amphetamine made by the Leuckart or nitrostyrene process.

Compare the cuprate-made amphetamine to the Leuckart or nitrostyrene-made amphetamine standard, which has one or more impurities:

cathinone 0.25 NMT limit w/w %, benzaldehyde 0.25 NMT limit w/w %, dextroamphetamine related cmpd A 0.25 NMT limit w/w %, dextroamphetamine related cmpd B 0.25 NMT limit w/w %, or unspecified impurity (formaldehyde) 0.1 NMT limit w/w %.

Perform a secondary confirmation of the cuprate-made amphetamine by performing an HPLC assay to identify impurity 6b.

The presence or absence of the [cathinone, benzaldehyde, related cmpd A or B, or unspecified/formaldehyde impurity], compared to the presence or absence of cuprate-process impurity 6b, identifies the process by which the amphetamine was made.

Additional Assay of Patient Sample

Obtain a sample, e.g. plasma, of a patient.

Perform a suitable assay for amphetamine.

Identify whether the sample contains an impurity of Compound 6b from the cuprate process or has one or more impurities from the Leuckart and/or nitrostyrene processes comprising [cathinone, benzaldehyde, related compound A or B, or unspecified/formaldehyde impurity].

Compare the sample results to a reference standard for the impurity of Compound 6b in the Cuprate Process and from the from the Leuckart and/or nitrostyrene processes comprising [cathinone, benzaldehyde, related compound A or B, or unspecified/formaldehyde impurity].

Identify whether the amphetamine from the sample was prepared using the cuprate process.

In another embodiment, the invention also includes a method for detection of amphetamine product in a sample, comprising the steps:

(i) performing an amphetamine assay on a plasma sample;

(ii) identifying whether the plasma sample contains an impurity from a cuprate process or has one or more impurities from a different amphetamine reaction process, said impurities comprising cathinone impurity 0.25 NMT limit w/w %, benzaldehyde impurity 0.25 NMT limit w/w %, related compound A or B impurity 0.25 NMT limit w/w %, respectively, or unspecified/formaldehyde impurity 0.1 NMT limit w/w %, wherein the cuprate process comprises preparing dextroamphetamine (sulfate) using a cuprate reaction of a phosphoramidate compound in the presence of a Grignard reagent, followed by hydroxide reduction of the alkyl side chain, followed by a first solvent crystallization in THF and heptanes, and a second solvent recrystallization in heptanes, made into a sulfate salt;

(iii) comparing the impurity in plasma sample results to a reference standard for the impurity in the cuprate process and from the different amphetamine process comprising cathinone, benzaldehyde, related compound A or B, or unspecified/formaldehyde impurity; and (v) identifying whether the amphetamine from the plasma sample was prepared using the cuprate process.

In preferred embodiments, the assays may be used when the cuprate process is used to make dextro amphetamine from L-alaninol, racemic amphetamine from either racemic alaninol or monoisopropanolamine, or levo amphetamine from D-alaninol, by converting converting alaninol to phosphoramidate, performing cuprate reaction of phosphoramidate in presence of Grignard and THF solvent, crystallizing in mixture of THF and Heptane solvents, re-crystallizing in heptanes to 98%+ purity, then comparing to amphetamine made by a different non-cuprate process to identify whether the amphetamine was made using the cuprate process or a different non-cuprate process.

The references recited herein are incorporated herein in their entirety, particularly as they relate to teaching the level of ordinary skill in this art and for any disclosure necessary for the commoner understanding of the subject matter of the claimed invention. It will be clear to a person of ordinary skill in the art that the above embodiments may be altered or that insubstantial changes may be made without departing from the scope of the invention. Accordingly, the scope of the invention is determined by the scope of the following claims and their equitable Equivalents.

What is claimed as the invention:

1. A process of making levoamphetamine sulfate, said process comprising:

preparing an in situ phenyl magnesium bromide from a reaction of bromobenzene with magnesium in the presence of catalytic diisobutyl aluminum hydride (DIBAL) in tetrahydrofuran (THF) refluxing at a temperature of 60 deg Celsius;

reacting a compound of Formula 4

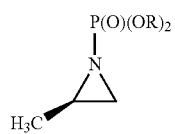

(Formula 4)

with the in situ phenyl magnesium bromide and a copper catalyst under solvent and temperature conditions effective to produce a compound of Formula 5 having a regioisomeric purity >99%:

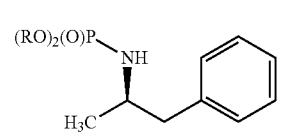

(Formula 5)

wherein R is alkyl or aryl; and
deprotecting the compound of Formula 5 at a temperature of 80 deg Celsius and under acidic conditions effective to produce levoamphetamine free base

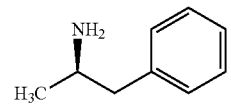

and then levoamphetamine sulfate of Formula I:

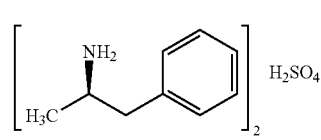

(Formula I)

wherein the solvent conditions for preparing the compound of Formula 5 comprise a crystallization step requiring a mixture of two or more solvents, wherein one of the two or more solvents is residue THF.

2. The process according to claim 1 wherein the acidic conditions are aqueous hydrochloric, sulfuric or phosphoric acids.

3. The process according to claim 2 wherein the aqueous acid water content is in an amount of 50% to 90%.

4. The process according to claim 1 wherein R=methyl, ethyl, isopropyl or phenyl.

5. The process according to claim 1 wherein the stereoisomeric purity of formula 5 is >99% and the stereoisomer is <0.1%.

6. The process according to claim 1 wherein the copper catalyst is CuCl, $CuCl_2$, CuBr CuF, $Cu(OAc)_2$, $Cu(acac)_2$, $Cu(OMe)_2$, Copper turnings or Copper nanoparticles.

7. The process according to claim 1 wherein one of the mixture of two or more solvents is selected from the group consisting of heptanes, an organic ether, 2-methyltetrahydrofuran, and toluene.

8. The process according to claim 1, wherein said providing a compound of Formula 4 comprises: providing a compound of Formula 3

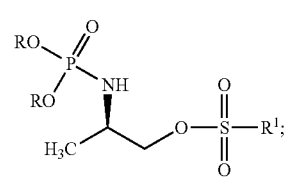

(Formula 3)

wherein R is alkyl or aryl; and R1 is alkyl or aryl or substituted aryl; and reacting a compound of Formula 3 with a base under conditions effective to produce a compound of Formula 4.

9. The process according to claim 8 where R1=alkyl, aryl, or substituted aryl.

10. The process according to claim 9 wherein the R1 is selected from methyl, phenyl or 4-methylphenyl.

11. The process according to claim 10 where R1 is methyl.

12. The process according to claim 11 wherein R is methyl, ethyl, isopropyl or phenyl.

13. The process according to claim 12, wherein the base is potassium hydroxide or potassium carbonate.

14. The process according to claim 13, wherein the step of providing a compound of Formula 3 comprises the steps of: providing a compound of Formula 2

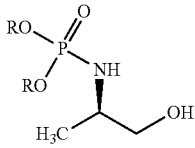
(Formula 2)

wherein R is alkyl or aryl; and reacting the compound of Formula 2 with an alkyl, aryl or substituted arylsulfonyl chloride and a base under conditions effective to produce a compound of Formula 3.

15. The process according to claim 14 wherein the R=methyl, ethyl, isopropyl or phenyl.

16. The process according to claim 14, wherein said providing a compound of Formula 2 comprises: providing a compound of Formula 1

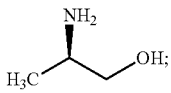
(Formula 1)

and reacting the compound of Formula 1 with

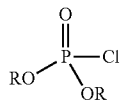

wherein R=alkyl or aryl under conditions effective to produce a compound of Formula 2.

17. The process according to claim 16 wherein the R is methyl, ethyl, isopropyl or phenyl.

18. The process according to claim 1, wherein the levo-amphetamine sulfate of Formula I:

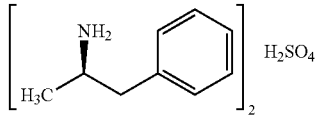
Formula I comprises a regiochemical purity of >1700:1.

19. The process according to claim 1, wherein the alkyl group is selected from the group consisting of methyl, ethyl or isopropyl.

20. The process according to claim 1, wherein the aryl group is phenyl.

* * * * *